US010391126B2

(12) United States Patent
Cooper et al.

(10) Patent No.: US 10,391,126 B2
(45) Date of Patent: Aug. 27, 2019

(54) CAR+ T CELLS GENETICALLY MODIFIED TO ELIMINATE EXPRESSION OF T-CELL RECEPTOR AND/OR HLA

(71) Applicant: Board of Regents, The University of Texas System, Austin, TX (US)

(72) Inventors: Laurence J. Neil Cooper, Houston, TX (US); Hiroki Torikai, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/358,828

(22) PCT Filed: Nov. 16, 2012

(86) PCT No.: PCT/US2012/065506
§ 371 (c)(1),
(2) Date: May 16, 2014

(87) PCT Pub. No.: WO2013/074916
PCT Pub. Date: May 23, 2013

(65) Prior Publication Data
US 2014/0349402 A1 Nov. 27, 2014

Related U.S. Application Data

(60) Provisional application No. 61/561,364, filed on Nov. 18, 2011.

(51) Int. Cl.
*A61K 35/14* (2015.01)
*A61K 35/17* (2015.01)
*A61K 39/00* (2006.01)
*C12N 5/0783* (2010.01)

(52) U.S. Cl.
CPC .......... *A61K 35/17* (2013.01); *A61K 39/0011* (2013.01); *C12N 5/0636* (2013.01); *A61K 2039/5156* (2013.01); *A61K 2039/5158* (2013.01); *C12N 2510/00* (2013.01); *Y02A 50/467* (2018.01)

(58) Field of Classification Search
None
See application file for complete search history.

(56) References Cited

U.S. PATENT DOCUMENTS

| 6,986,887 | B2 * | 1/2006 | Lawman | C07K 14/70539 424/93.2 |
|---|---|---|---|---|
| 7,833,706 | B2 | 11/2010 | Begovich et al. | |
| 7,888,121 | B2 † | 2/2011 | Urnov | |
| 8,945,868 | B2 † | 2/2015 | Collingwood | |
| 8,956,828 | B2 † | 2/2015 | Bonini | |
| 2003/0194704 | A1 | 10/2003 | Penn et al. | |
| 2007/0036773 | A1 * | 2/2007 | Cooper | A61K 48/00 424/93.21 |
| 2007/0283453 | A1 | 12/2007 | Cimadevilla | |
| 2009/0197309 | A1 | 8/2009 | Sycheva et al. | |
| 2009/0258363 | A1 | 10/2009 | Gregory | |
| 2011/0158957 | A1 * | 6/2011 | Bonini | C12N 9/22 424/93.7 |
| 2012/0060230 | A1 | 3/2012 | Collingwood et al. | |
| 2012/0277120 | A1 * | 11/2012 | Serber | C12N 15/905 506/14 |

FOREIGN PATENT DOCUMENTS

WO   WO 2011-059836   5/2011

OTHER PUBLICATIONS

Motmans et al., Enhancing the tumor-specifity of human T cells by the expression of chimeric immunoglobulin/T cell receptor genes. Immunotechnology 2(4) Dec. 1995, pp. 303-304.*
Kowolik et al., CD28 Costimulation Provided through a CD19-Specific Chimeric Antigen Receptor Enhances In vivo Persistence and Antitumor Efficacy of Adoptively Transferred T Cells. Cancer Res 2006; 66: (22). Nov. 15, 2006, pp. 10995-11004.*
Davies et al., Combining CD19-redirection and alloanergization to generate tumor-specific human T cells for allogeneic cell therapy of B-cell malignancies. Cancer Res. May 15, 2010; 70(10): 3915-3924.*
Huang et al., Sleeping Beauty transposon-mediated engineering of human primary T cells for therapy of CD19+ lymphoid malignancies. Mol Ther. Mar. 2008;16(3):580-9.*
Ehlers et al., "Alphabeta T cell receptor-positive cells and interferon-gamma, but not inducible nitric oxide synthase, are critical for granuloma necrosis in a mouse model of mycobacteria-induced pulmonary immunopathy", *The Journal of Experimental Medicine*, 194(12):1847-1859, 2001.
Gascoignet, "Transport and secretion of truncated T cell receptor and chamin occurs in the absence of association with CD3", *The Journal of Biological Chemistry*, 265(16):9296-9301, 1990.
PCT International Preliminary Report on Patentability issued in International Application No. PCT/US2012/065506, dated May 30, 2014.
PCT International Search Report and Written Opinion issued in International Application No. PCT/US2012/065506, dated Mar. 4, 2013.
Torikai et al., "A foundation for universal T-cell based immunotherapy: T cells engineered to express a CD19-specific chimeric-antigen-receptor and eliminate expression of endogenous TCR", *Blood*, 119(24):5697-5705, 2012.

(Continued)

*Primary Examiner* — Scott Long
*Assistant Examiner* — Arthur S Leonard
(74) *Attorney, Agent, or Firm* — Parker Highlander PLLC

(57) ABSTRACT

The present invention concerns methods and compositions for immunotherapy employing a modified T cell comprising disrupted T cell receptor and/or HLA and comprising a chimeric antigen receptor. In certain embodiments, the compositions are employed allogeneically as universal reagents for "off-the-shelf treatment of medical conditions such as cancer, autoimmunity, and infection. In particular embodiments, the T cell receptor-negative and/or HLA-negative T cells are generated using zinc finger nucleases, for example.

14 Claims, 24 Drawing Sheets

Specification includes a Sequence Listing.

(56) References Cited

OTHER PUBLICATIONS

Torikai et al., "HLA and TCR Knockout by Zinc Finger Nucleases: Toward "off-the-Shelf" Allogeneic T-Cell Therapy for CD19+ Malignancies", 53rd ASH Annual Meeting and Exposition, Abstract 3766, 2011.
Beerli and Barbas, "Engineering polydactyl zinc-finger transcription factors", Nature Biotechnol., 20:135-141, 2002.
Beurdeley et al., "Compact designer TALENs for efficient genome engineering", Nature Communications, 4:1762 doi: 10.1038/ncomms2782, 2013.
Boch et al., "Breaking the code of DNA binding specificity of TAL-type III effectors", Science, 326: 1509-1512, 2009.
Boissel et al., "megaTALs: a rare-cleaving nuclease architecture for therapeutic genome engineering", Nucleic Acids Research, 42(4): 2591-2601, 2014.
Bonas et al., "Genetic and structural characterization of the avirulence gene avrBs3 from Xanthomonas campestris pv. vesicatoria", Mol Gen Genet., 218: 127-136, 1989.
Borrego et al., "Recognition of human histocompatibility leukocyte antigen (HLA)-E complexed with HLA class I signal sequence-derived peptides by CD94/NKG2 confers protection from natural killer cell-mediated lysis", J Exp Med., 187(5): 813-8, 1998.
Braud et al., "HLA-E binds to natural killer cell receptors CD94/NKG2A, B and C", Nature, 391: 795-799, 1998.
Bukur et al., "The role of classical and non-classical HLA class I antigens in human tumors", Seminars in Cancer Biology, 22: 350-358, 2012.
Choo and Isalan, "Advances in zinc finger engineering", Curr Opin Struct Biol., 10(4): 411-6, 2000.
Cohen et al., "In vivo expression of MHC class I genes depends on the presence of a downstream barrier element", PLoS ONE, 4(8): e6748. Doi:10.1371/journal.pone.0006748, 2009. Figure 1.
Fehling et al., "MHC class I expression in mice lacking the proteasome subunit LMP-7", Science, 265(5176): 1234-7, 1994.
Garbi et al., "Impaired immune responses and altered peptide repertoire in tapasin-deficient mice", Nature Immunology, 1(3): 234-8, 2000.
Grandea et al., "Impaired assembly yet normal trafficking of MHC class I molecules in Tapasin mutant mice", Immunity, 13: 231-222, 2000.
Guschin et al., "A rapid and general assay for monitoring endogenous gene modification", in Engineered Zinc Finger Proteins, eds. Mackay and Segal, Ch. 15, pp. 247-256, 2010.
Haft et al., "A guild of 45 CRISPR-Associated (Cas) protein families and multiple CRISPR/Cas subtypes exist in prokaryotic genomes", PLoS Comput Biol., 1(6): e60, 2005.
Heuer et al., "Repeat domain diversity of avrBs3-like genes in Ralstonia solanacearum strains and association with host preferences in the field", Appl. Environ. Microbiol., 73(13): 4379-4384, 2007.
Hockemeyer et al., "A drug-inducible system for direct reprogramming of human somatic cells to pluripotency", Cell Stem Cell, 3: 346-353, 2008.
Isalan et al., "A rapid, generally applicable method to engineer zinc fingers illustrated by targeting the HIV-1 promoter", Nat Biotechnol., 19(7): 656-660, 2001.
Jansen et al., "Identification of genes that are associated with DNA repeats in prokaryotes", Molecular Microbiology, 43(6): 1565-1575, 2002.
Kageshita et al., "Down-regulation of HLA class I antigen-processing molecules in malignant melanoma", American Journal of Pathology, 154(3): 745-754, 1999.
Kalos et al., "T cells with chimeric antigen receptors have potent antitumor effects and can establish memory in patients with advanced letikemia", Sci Transl Med., 3: 95ra73, 2011.
Kay el al., "A bacterial effector acts as a plant transcription factor and induces a cell size regulator", Science, 318(5850): 648-51, 2007. Supporting Material.

LeibundGut-Landmann et al., "Specificity and expression of CIITA, the master regulator of MHC class II genes", Eur. J. Immunol., 34: 1513-1525, 2004.
Maier et al., "High-resulution HLA alleles and haplotypes in the United States population", Human Immunology, 68: 779-788, 2007.
Makarova et al., "A DNA repair system specific for thermophilic archaea and bacteria predicted by genomic context analysis", Nucleic Acids Research, :30(2): 482-496, 2002.
Makarova et al., "A putative RNA-interference-based immune system in prokaryotes: computational analysis of the predicted enzymatic machinery, functional analogies with eukaryotic RNAi, and hypothetical mechanisms of action", Biology Direct, 1:7, 2006.
Manuri et al., "piggyback transposon/transposase system to generate CD19-specific T cells for the treatment of B-lineage malignancies", Human Gene Therapy, 21: 427-437, 2010.
Moscou and Bogdanove, "A simple cipher governs DNA recognition by TAL effectors", Science, 326: 1501, 2009.
O'Conner et al., "Adoptive T-cell therapy improves treatment of canine non-Hodgkin lymphoma post chemotherapy", Sci Rep., 2: 249, 2012.
Patio et al., "Design and selection of novel $Cys_2His_2$ zinc finger proteins", Annu. Rev. Biochem., 70: 313-40, 2001.
Parham, "MHC class I molecules and KIRS in human history, health and survival", Nature Reviews immunology, 5: 201-214, 2005.
Porter et al., "Chimeric antigen receptor-modified T cells in chronic lymphoid leukemia", The New England Journal of Medicine, 365(8): 725-733, 2011.
Provasi et al., "Editing T cell specificity towards leukemia by zinc finger nucleases and lentiviral gene transfer", Nature Medicine, 18(5): 807-815, 2012.
Riteau et al., "HLA-G1 co-expression boosts the HLA class I-mediated NK lysis inhibition", International Immunology, 13(2): 193-201, 2001.
Rouas-Freiss et al., "The $\alpha_1$ domain of HLA-G1 and HLA -G2 inhibits cytotoxicity induced by natural killer cells: is HLA-G the public ligand for natural killer cell inhibitoty receptors?", Proc. Natl. Acad. Sci. USA, 94: 5249-5254, 1997.
Schornack et al., "Gene-for-gene-mediated recognition of nuclear-targeted AvrBs3-like bacterial effector proteins", Journal of Plant Physiology, 163: 256-272, 2006.
Segal and Barbas, "Customs DNA-binding proteins come of age: polydactyl zinc-finger proteins", Current Opinion in Biotechnology, 12: 632-637, 2001.
Singh et al., "Redirecting specificity of T-cell populations for CD19 using the Sleeping Beauty system", Cancer Res., 68(8): 2961-2971, 2008.
Villard et al., "A functionally essential domain of RFX5 mediates activation of major histocompatibility complex class II promoters by promoting cooperative binding between RFX and NF-Y", Molecular and Cellular Biology, 20(10): 3364-3376, 2000.
Zhu et al., "Overexpression of miR-152 leads to reduced expression of human leukocyte antigen-G and increased natural killer cell mediated cytolysis in JEG-3 cells", Am J Obstet Gynecol., 202(6): 592. e1-7, 2010.
"Human leukocyte antigen", Wikipedia, downloaded on Jun. 3, 2016.
Collin et al., "Concise review: putting a finger on stem cell biology: zinc finger nuclease-driven targeted genetic editing in human pluripotent stem cells", Stem Cells 19: 1021-1033, 2011.
Holmes et al., "Disruption of HLA expression to enable allogeneic cells to escape immune recognition", Human Gene Therapy, 22(10): Or 15, 2011. p. A25-A26.
Jamieson et al., "Drug discovery with engineered zinc-finger proteins", Nature Reviews Drug Discovery,, 2(5): 361-368, 2003.
L 'Haridon et al., "Transcriptional regulation of the MHC class I HLA-A11 promoter by the zinc finger protein ZFX", Nucleic Acids Research, 24(10): 1928-1935, 1996.
Torikai et al., "HLA and TCR knockout by zinc finger nucleases: toward "off-the-shelf" allogeneic t-cell therapy for CD19+ malignancies", Blood (ASH Annual Meeting Abstracts), 116: Abstract 3766, 2010.

(56) References Cited

OTHER PUBLICATIONS

Torikai et al., "Toward eliminating HLA class I expression to generate universal cells from allogeneic donors", *Blood,* 122(8): 1341-1349, 2013.
Foroni et al., "HLA-E, HLA-F, and HLA-G—the non-classical side of the MHC cluster", *HLA and associated important diseases,* Yongzhi Xi (Ed), InTech, DOI: 10.5772/57507, Chapter 3, 2014.
Office Communication issued in U.S. Appl. No. 14/206,706, dated Oct. 12, 2016.

\* cited by examiner
† cited by third party

CAR+ T CELLS GENETICALLY MODIFIED TO ELIMINATE EXPRESSION OF T-CELL RECEPTOR AND/OR HLA

The present application is a national phase application under 35 U.S.C. § 371 of International Application No. PCT/US2012/065506, filed Nov. 16, 2012, which claims the priority benefit of U.S. provisional application No. 61/561,364, filed Nov. 18, 2011, the entire contents of each of which are incorporated herein by reference.

This invention was made with government support under Grant No. PR064229, awarded by the Department of Defense, and Grant Nos. CA124782, CA120956, CA141303, and CA116127, awarded by the National Institutes of Health. The government has certain rights to the invention.

SEQUENCE LISTING

The instant application contains a Sequence Listing which has been submitted electronically in ASCII format and is hereby incorporated by reference in its entirety. Said ASCII copy, created on Jul. 20, 2016, is named 0100-019US1_SL.txt and is 2,218 bytes in size.

BACKGROUND OF THE INVENTION

1. Field of the Invention

The field of the invention includes at least medicine, immunology, cell biology, and molecular biology. In certain aspects the field of the invention includes immunotherapy.

2. Description of Related Art

Allogeneic hematopoietic stem-cell transplantation (HSCT) can cure some patients with high risk B-cell leukemia/lymphoma, but relapse remains a major cause of death. To improve the graft-versus-leukemia/lymphoma (GVL)-effect, donor-derived T cells can be genetically modified to express a tumor-specific chimeric antigen receptor (CAR) with specificity derived, for example, from the variable domains of a monoclonal antibody, thus focusing immunoreactivity towards the tumor in an MHC non-restricted manner (Cooper et al., 2004). However, the endogenous $\alpha\beta$ T-cell receptor (TCR) on infused allogeneic T cells may recognize major and minor histocompatibility antigens in the recipient, leading to graft-versus-host-disease (GVHD). As a result, the majority of current clinical trials infuse autologous $CAR^+$ T cells relying on immune tolerance to prevent TCR-mediated deleterious recognition of normal tissues after adoptive transfer (Jena et al., 2010). This approach has achieved early clinical successes (Kochenderfer et al., 2010), but is limited by the time and expense to manufacture patient-specific T-cell products.

CD19 is constitutively expressed on most acute and chronic B-cell malignancies. Therefore, to target malignant B cells, the Sleeping Beauty (SB) transposon/transposase system was adapted for human application, e.g., to stably express a CD19-specific CAR (designated CD19RCD28) (Kohn et al., 2011; Izsvak et al., 2010; Hackett et al., 2010; Williams, 2008; see U.S. Pat. No. 6,489,458, incorporated by reference herein in its entirety). SB modified $CAR^+$ T cells can be numerically expanded to clinically-sufficient numbers by the recursive addition of γ-irradiated designer artificial antigen presenting cells (aAPC) that co-express CD19 and desired T-cell co-stimulatory molecules (Singh et al., 2008; Davies et al., 2010). This has been adapted for clinical translation at M.D. Anderson Cancer Center, as four clinical trials based on the electroporation and propagation of $CAR^+$ T cells have achieved institutional and federal regulatory approvals for the adoptive transfer of $CD19RCD28^+$ T cells after autologous and allogeneic hematopoietic stem-cell transplantation (e.g., IND #14193, ClinicalTrials.gov Identifier: NCT00968760) (Jena et al., 2010; Kohn et al., 2011; Hackett et al., 2010; Williams, 2008). However, a need in the art remains to develop methods and reagents that circumvent the time and expense to manufacture patient-specific T-cell products.

SUMMARY OF THE INVENTION

The present invention is directed to methods and/or compositions for use in medicine, for example, for use in immunotherapy, including immunotherapy for infection or cancer, for example. In some embodiments, there is provided universal T cell-based immunotherapy including T cells engineered to express an antigen-specific chimeric antigen receptor (CAR) and to eliminate expression of endogenous alpha/beta T-cell receptor (TCR). In specific embodiments, there are CAR+ T cells genetically modified to eliminate expression of TCR.

In some embodiments, there is disruption of the T-cell receptor $\alpha/\beta$ in CAR-expressing T cells using zinc finger nucleases (ZFNs) for generating universal T cells for immunotherapy. In embodiments of the invention, there is knocking out of the T-cell receptor $\alpha\beta$-chain in CAR-expressing T cells, for example using zinc finger nucleases.

In some embodiments, there are universal CAR-expressing T cells, such as from a healthy donor, that may be suitably stored, for example, in the freezer, and then infused into allogeneic individuals on demand. This allows interested parties to prepare and validate genetically modified antigen-specific T cells before individuals need them. These T cell products significantly broaden the application of antigen-specific T-cell therapy, such as for cancer and infection, for example. In certain embodiments, the invention provides off-the-shelf universal $CAR^+$ T cells from allogeneic healthy donors that can be administered to any patient without causing GVHD. An advantage to the methods and compositions of the present invention is that the modified cells allow interrogation of the antigen independence of MHC and therefore the cells are suitable for any genetic background in the recipient. However, in some embodiments, the $CAR^+TCR^{neg}$ cells are autologous.

Any kind of autoimmune disease, infection, and cancer can be treated with methods and/or compositions of the invention, including primary, metastatic, recurrent, sensitive-to-therapy, refractory-to-therapy, and so forth. In some embodiments, the methods and/or compositions are employed for chemo-refractory cancer. The cancer may be of the blood, lung, brain, colon, prostate, breast, liver, kidney, stomach, cervix, ovary, testes, pituitary gland, esophagus, spleen, skin, bone, and so forth.

The skilled artisan recognizes that in some methods there is simple depletion of T cells that continue to express TCR by using, for example, clinical-grade CD3-specific monoclonal antibody such that a T-cell product can be generated in which at least the majority have lost expression of endogenous TCR. Other ways include the use of fluorescence-activated cell sorting (FACS) and TCR-specific monoclonal antibodies or aptamers to reduce and possibly eliminate the presence of T cells that continue to express TCR. In addition, TCR-specific antibodies can be combined with other purification schemes, such as addition of complement, toxins, or resetting to reduce/eliminate T cells that continue to express TCR.

In certain embodiments there are methods of treating an individual in need of treatment using compositions encompassed by the invention. The treatment includes employing particular T cells having a CAR and also having genetic modifications to exclude functional TCR. Although in specific embodiments the modifications of the cells exclude functional TCR by any suitable means, in certain aspects the modifications include knock out (or in alternative embodiments, knock down, such as by siRNA and TALENs, for example) of the α and/or β chains or the gamma and/or delta chains of the TCR.

In some embodiments, there is a method of making a cell expressing a CAR comprising introducing an expression cassette in to the cell, wherein the expression cassette encodes a polypeptide comprising a heterologous human extracellular antigen binding domain, a transmembrane domain, and one or more an intracellular signaling domain(s). In some embodiments, the methods further comprise stimulating the cells with antigen presenting cells, recombinant antigen, or an antibody to the receptor to cause the cells to proliferate, kill, and/or make cytokines. In specific embodiments, the method further comprises stimulating the cells with antigen presenting cells to cause the cells to proliferate.

In some embodiments, there are recombinant antigen-specific TCR cells expressing and bearing on the cell surface membrane an antigen-specific CAR human polypeptide comprising an intracellular signaling domain, a transmembrane domain and an extracellular domain, the extracellular domain comprising a human anti-antigen monoclonal antibody or antigen binding fragment thereof.

In some embodiments, there is a method of treating a human disease condition associated with a cell expressing endogenous CD19 comprising infusing a patient with an amount of a recombinant TCR$^{neg}$ cell expressing a human antigen-specific CAR (such as CD19-specific) sufficient to treat the condition, wherein the human antigen-specific CAR comprises a heterologous human CD19 extracellular binding domain, a transmembrane domain, and an intracellular signaling domain.

In some embodiments more than one pair of zinc finger nucleases can be used to modify a cell. For example, both zinc finger nucleases targeting the alpha chain and the beta chain can be used to eliminate T-cell receptor expression. In another instance, the zinc finger nucleases targeting the T-cell receptor can be used (for example, sequentially) with zinc finger nucleases to target one or more human leukocyte antigen(s) (HLA). This is desirable to generate universal T cells that have lost not only T-cell receptor expression, but also HLA expression, and thus will be less susceptible to immune-mediated recognition from the allogeneic recipient and thus targeted for destruction.

In one embodiment there is an isolated T-cell population wherein cells of the population comprise an endogenous T-cell receptor coding sequence that is either not expressed or which encodes a nonfunctional T-cell receptor; and a recombinant chimeric antigen receptor comprising an intracellular signaling domain, a transmembrane domain, and an extracellular domain comprising an antigen binding region. In specific embodiments, the T-cell receptor is nonfunctional by virtue of one or more disruptions in the coding sequence of α chain, β chain, or both. In some embodiments, the endogenous T-cell receptor is knocked out. In specific embodiments, the antigen binding region is an F(ab')2, Fab', Fab, Fv, or scFv and/or the antigen binding region binds a tumor associated antigen, such as CD19, CD20, ROR1, carcinoembryonic antigen, alphafetoprotein, CA-125, MUC-1, epithelial tumor antigen, melanoma-associated antigen, mutated p53, mutated ras, HER2/Neu, ERBB2, HER3, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, IL-13Ralpha2, kappa chain, or lambda chain, CSPG4 (also known as, high molecular weight melanoma associated antigen), EGFRvIII, and VEGFR2. In specific embodiments, the antigen binding region binds a pathogen antigen, such as a fungal, viral, or bacterial antigen. In some cases, the fungal antigen is from *Aspergillus* or *Candida*. In certain cases, the viral antigen is from HSV, RSV, EBV, CMV, JC virus, BK virus, or Ebola.

In embodiments of the invention, there is an intracellular signaling domain that is a T-lymphocyte activation domain. In some embodiments, the intracellular signaling domain comprises CD3ζ, CD28, OX40/CD134, 4-1BB/CD137, FcεRIγ, ICOS/CD278. ILRB/CD122, IL-2RG/CD132, DAP molecules, CD70, cytokine receptor, CD40, or a combination thereof.

In certain embodiments, the transmembrane domain comprises IgG4Fc hinge, Fc regions, CD4 transmembrane domain, CD28 transmembrane domain, the CD3ζ transmembrane domain, cysteine mutated human CD3ζ domain, CD16 transmembrane domain, CD8 transmembrane domain, or erythropoietin receptor transmembrane domain.

In some embodiments, there is an exemplary chimeric antigen receptor that comprises: a) an antigen binding domain from a variable region of an antigen-specific monoclonal antibody; b) a signaling domain of CD3ζ and c) CD28, CD137, CD134, or combinations thereof.

In some cases, there are methods of generating the cells of the invention, comprising the steps of: a) providing one or more T cells; b) modifying the T cell(s) to express a recombinant chimeric antigen receptor comprising an intracellular signaling domain, a transmembrane domain, and an extracellular domain comprising an antigen binding region, and c) modifying the T cell(s) to harbor an endogenous T-cell receptor coding sequence that is not expressed or encodes a nonfunctional T-cell receptor. In specific embodiments, step b) occurs before step c) or step c) occurs before step b). In certain aspects, the T cell is provided from an umbilical cord blood bank, is provided from a peripheral blood bank, is an induced pluripotent stem cell, or is a human embryonic stem cell. In some cases, the T cell is allogeneic in reference to one or more intended recipients.

In some embodiments, the chimeric antigen receptor is stably introduced into the cell, and in certain embodiments, the polynucleotide that encodes the chimeric antigen receptor is introduced into the cell by a transposon/transposase system or a viral-based gene transfer system, such as by recombinant retrovirus or lentivirus.

In some embodiments, following modification of the T cell(s), they are propagated by exposing the T cells to artificial antigen presenting cells, by using OKT3 (or equivalent to cross-link CD3) optionally with other co-stimulatory antibodies (e.g., anti-CD28) on beads, or by using OKT3 (or equivalent to cross-link CD3) optionally with other co-stimulatory antibodies (e.g., anti-CD28) mixed with peripheral blood mononuclear cells. In specific aspects, a polynucleotide that encodes the recombinant chimeric antigen receptor is electroporated into the T cell. In some embodiments, a polynucleotide that encodes the chimeric antigen receptor is present on a plasmid or viral vector.

In some embodiments, the T cell can be genetically modified with zinc finger nuclease or TLAE nuclease to eliminate HLA expression. The T cell may express a CAR and/or have been modified to eliminate TCR expression.

In some embodiments, the endogenous T-cell receptor and/or HLA is disrupted by nonhomologous end joining repair, such as is generated by zinc finger nuclease, TALE nuclease, introduced into the cell by physical means, electro-transfer of mRNA species, viral vector, or non-viral vector.

In some embodiments, there are methods of treating an individual with a medical condition (such as autoimmune disease, cancer, or infection, including *Aspergillus* or *Candida*), comprising the step of providing an effective amount of cells from the population of cells described herein, including more than once in some aspects, such as at least 1, 2, 3, 4, 5, 6, 7, 8, 9, 10, 11, 12, 13, 14, or more days apart. In specific embodiments, the cancer is lymphoma, leukemia, non-Hodgkin's lymphoma, acute lymphoblastic leukemia, chronic lymphoblastic leukemia, chronic lymphocytic leukemia, or B cell-associated autoimmune diseases.

The foregoing has outlined rather broadly the features and technical advantages of the present invention in order that the detailed description of the invention that follows may be better understood. Additional features and advantages of the invention will be described hereinafter, which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

Figure 1:
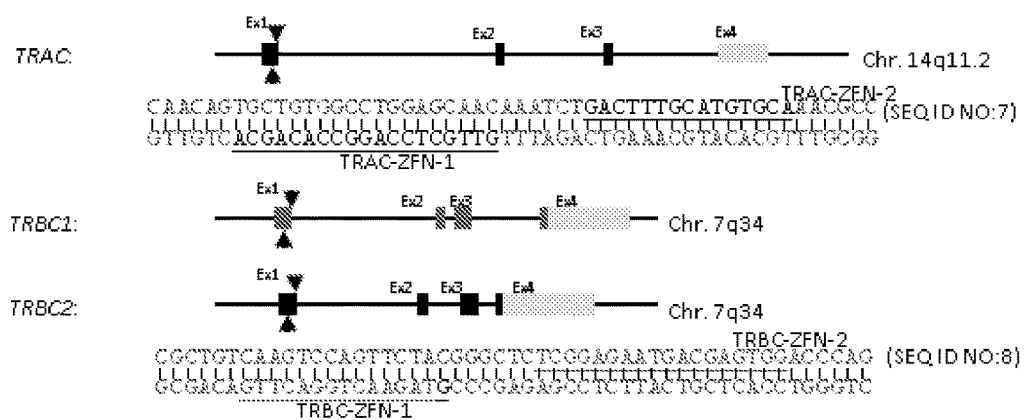
FIG. 1. ZFN pairs targeting sites within genomic loci of TCR-α and β constant region. Each exon is shown by a block. Black blocks represent coding regions. Grey columns represent non-coding regions. One ZFN pair was designed to bind exon 1 of the TCR α constant region (TRAC) and another ZFN pair binds a conserved sequence on exon 1 of the TCR β constant regions 1 (TRBC1) and 2 (TRBC2). Underlined nucleotide sequences represent the intended binding sequence of each ZFN.

a. Schematic Presentation of ZFN Transfer.

A pair of ZFN-encoding mRNA was electro-transferred into T cells six days after stimulation of $CAR^{neg}$ T cells. T cells were then cultured with 50 IU/mL of IL-2 and some cells were incubated at 30° C.-5% $CO_2$. CD3ε expression was analyzed on days 7-9 after electroporation by flow cytometry.

b. Down Regulation of CD3 after Electro-Transfer of ZFN Targeting TCR αβ from mRNA.

Day 9 after electro-transfer of graded doses of mRNA coding for pairs of ZFN, TCR αβ-CD3 expression was analyzed by co-staining for CD4, CD8, and CD3ε. The representative flow data at day nine after ZFN electro-transfer is shown. Flow cytometry data are gated on cells excluding propidium iodide. Numbers in the lower right quadrant represent the percentage of CD3ε negative cells in T-cell populations.

Top panels shows CD3ε expression in T cells cultured at 37° C. after ZFN transfer and bottom panels shows CD3ε expression in T cells transiently cultured at 30° C. from days 2-3 after ZFN transfer.

c. Surveyor Nuclease Assay to Detect ZFN-Mediated Modification of TCR Target Sites in T-Cells.

Arrows indicate the Cel-1 digested products after electro-transfer of graded doses of mRNA species. The numbers below the lanes represent percentages of target disruption in each sample.

FIG. 3. $TCR^{neg}$ T cells can be enriched by depletion of $CD3\varepsilon^+$ T cells.

a. CD3 Expression Before and after Depletion.

Representative results using in vitro expanded T cells. Flow cytometry revealing expression of CD3ε in $CD4^+$ and $CD8^+$ T cells. Numbers in the lower right quadrant represent the percentage of CD3ε-negative cells in T-cell populations.

b. Vβ Repertoire Analysis in T Cells Modified with ZFN.

The Vβ usage clonogram was analyzed by a panel of TCR-specific mAbs, co-stained with CD4 and CD8. Percentage of specific $V\beta^+$ T-cell fractions within CD4 and CD8 gating is shown. The nomenclatures of Vβ repertoire shown are based on Arden et al. (1995).

FIG. 4. Elimination of TCR αβ-CD3 complex from CD19-specific $CAR^+$ T cells.

a. Schematic of Electro-Transfer of mRNA Coding for ZFN Pairs in $CAR^+$ T Cells.

mRNAs coding for ZFN pairs were electro-transferred into $CAR^+$ T cells. A pair of ZFN was electro-transfer to T cells two days after stimulation with $CD19^+$ aAPC. After electroporation, cells were maintained with 50 IU/mL of IL-2 and incubated for two days at 30° C.-5% $CO_2$. CD3ε expression was analyzed nine days after electroporation by flow cytometry.

b. Disruption of TCR αβ-CD3 Complex Expression after Electro-Transfer of mRNA Coding for ZFN.

Flow cytometry analysis of CD3ε expression in T cells nine days after electro-transfer of mRNA species coding for ZFN is gated on propidium iodide negative.

c. Surveyor Nuclease Assay

Arrows indicate the Cel-1 digested products analyzed nine days after electroporation. The numbers at the bottom represent percentages of target disruption.

FIG. 5. Functional consequences of TCR knockout in $CAR^+$ T cells.

a. Loss of Responsiveness of $TCR^{neg}$ $CAR^+$ T Cells to TCR Stimulation.

Dilution of PKH26 was measured 10 days after stimulation with aAPC loaded with OKT3 (upper panel) or expressing CD19 (lower panel). Flow cytometry data was gated on $CAR^+$ T cells. Parental: $CAR^+$ T cells without modification; no mRNA: mock electroporated $CAR^+$ T cells; TRAC $CD3^{neg}$: $CAR^+$ T cells electroporated with mRNA coding for ZFN pairs specific for TRAC, and depleted $CD3^{pos}$ population; TRBC $CD3^{neg}$: $CAR^+$ T cells electroporated with mRNA coding for ZFN pairs specific for TRBC, and depleted for $CD3^{pos}$ population.

b. Redirected Specificity of TCR$^{neg}$ CAR$^+$ T Cells.

Specific lysis by CAR$^+$ T cells of an EL4 mouse T-cell line modified to express a truncated version of human CD19 (closed symbols) was measured by standard four hour $^{51}$Cr release assay. Specificity is shown by lack of lysis of CD19$^{neg}$ (parental) EL4 cells (open symbols). CAR$^+$ T cells were modified by ZFNs (TRAC and TRBC) or not modified by ZFNs (parental and no mRNA).

Figure 6:
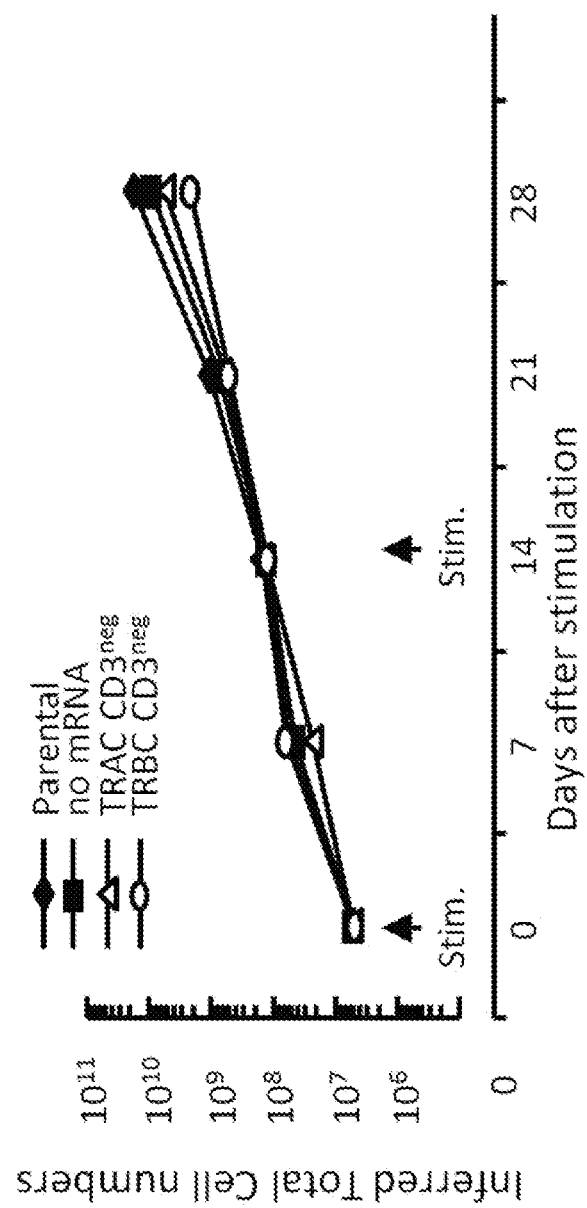

FIG. 6. Sustained proliferation of TCR$^{neg}$ CAR$^+$ T cells.

CAR$^+$ T cells with (TRAC and TRBC) or without (parental and no mRNA) TCR modification by ZFNs were stimulated with γ-irradiated CD19$^+$ aAPC every two weeks. Viable T cells were enumerated every seven days and inferred total numbers were calculated.

FIG. 7. Schematic of the approach to genetically modify and propagate T cells from PBMC. (a) T cells were propagated by stimulation with OKT3 loaded γ-irradiated aAPC (clone #4) in the presence of soluble IL-2. (b) DNA plasmids coding for SB transposon (CD19RCD28) and SB transposase (SB 1) were electro-transferred into primary human T cells. CAR$^+$ T cells were selectively propagated by repeated additions of γ-irradiated aAPC (clone #4) in the presence of rhIL-2.

Figures 8A, 8B:
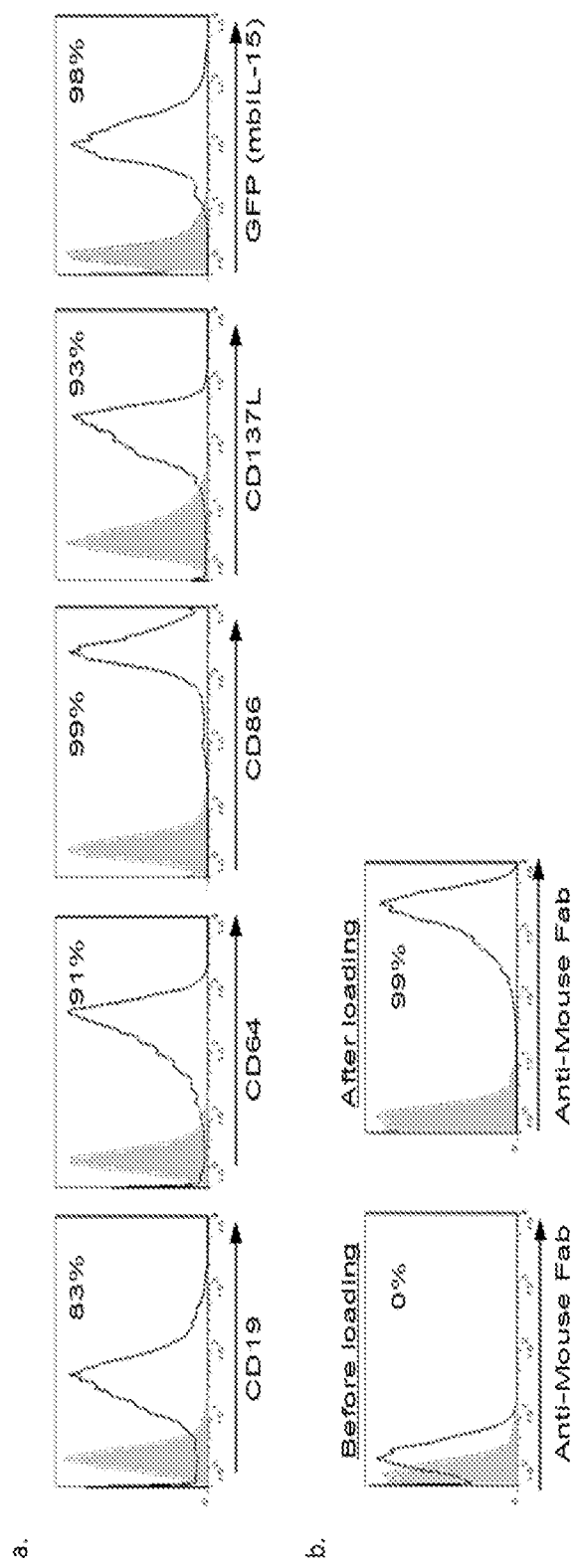

FIG. 8. Characterization of aAPC clone #4. (a) Flow cytometry was used to compare expression of CD19, CD64, CD86, CD137L, and MBIL-15 between parental K562 (grey shaded histogram) and K562-aAPC clone #4 (black open histogram). MBIL-15 is composed of human IL-15 peptide fused to modified human IgG4 Fc region and CD4 transmembrane domain and was detected by presence of EGFP (co-expressed with MBIL-15 after IRES element), aAPC were used to co-culture T cells if expression of introduced transgenes were >80%. (b) OKT3 was loaded onto aAPC clone #4 at 1 µg per 10$^6$ cells. Flow cytometry data before and after OKT3 loading detected by antibody specific for mouse Fab region. No-staining control: grey shaded histogram; stain with anti-mouse Fab: black open histogram.

Figure 9:
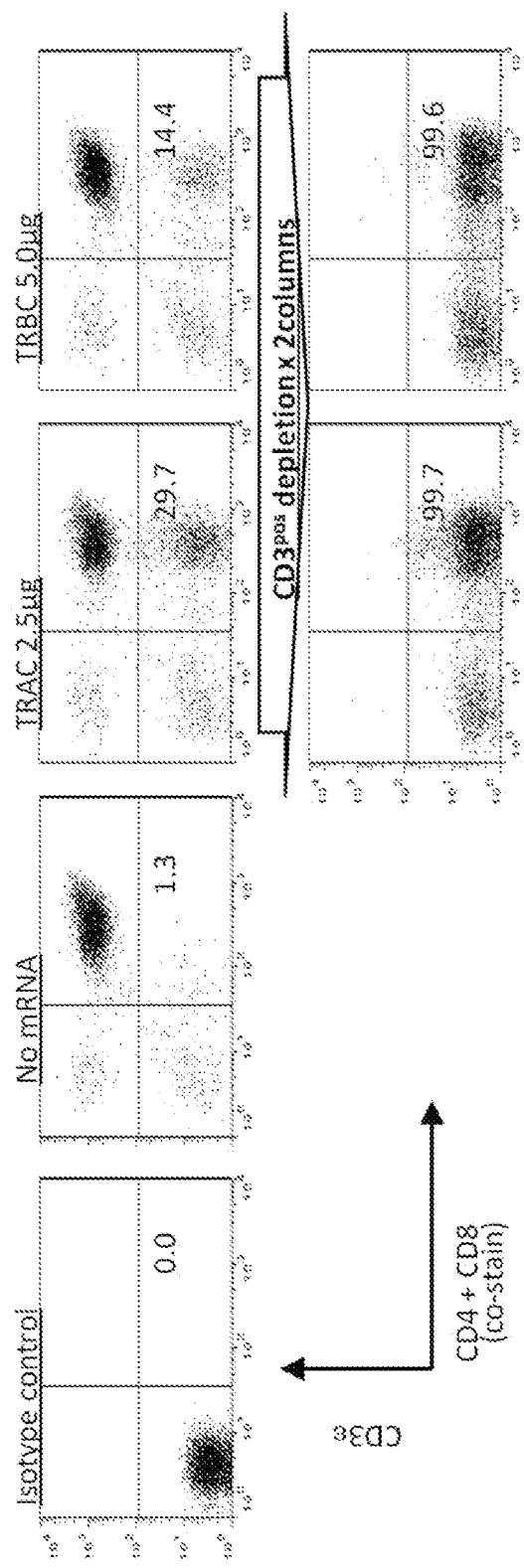

FIG. 9. Depletion of a CD3ε-positive population. Representative results from multiple experiments using in vitro expanded T cells. Flow cytometry revealing expression of CD3ε in CD4$^+$ and CD8$^+$ T cells. Numbers in the lower right quadrant represent the percentage of CD3ε-negative cells in CD4$^+$ and CD8$^+$ T-cell populations.

Figure 10:
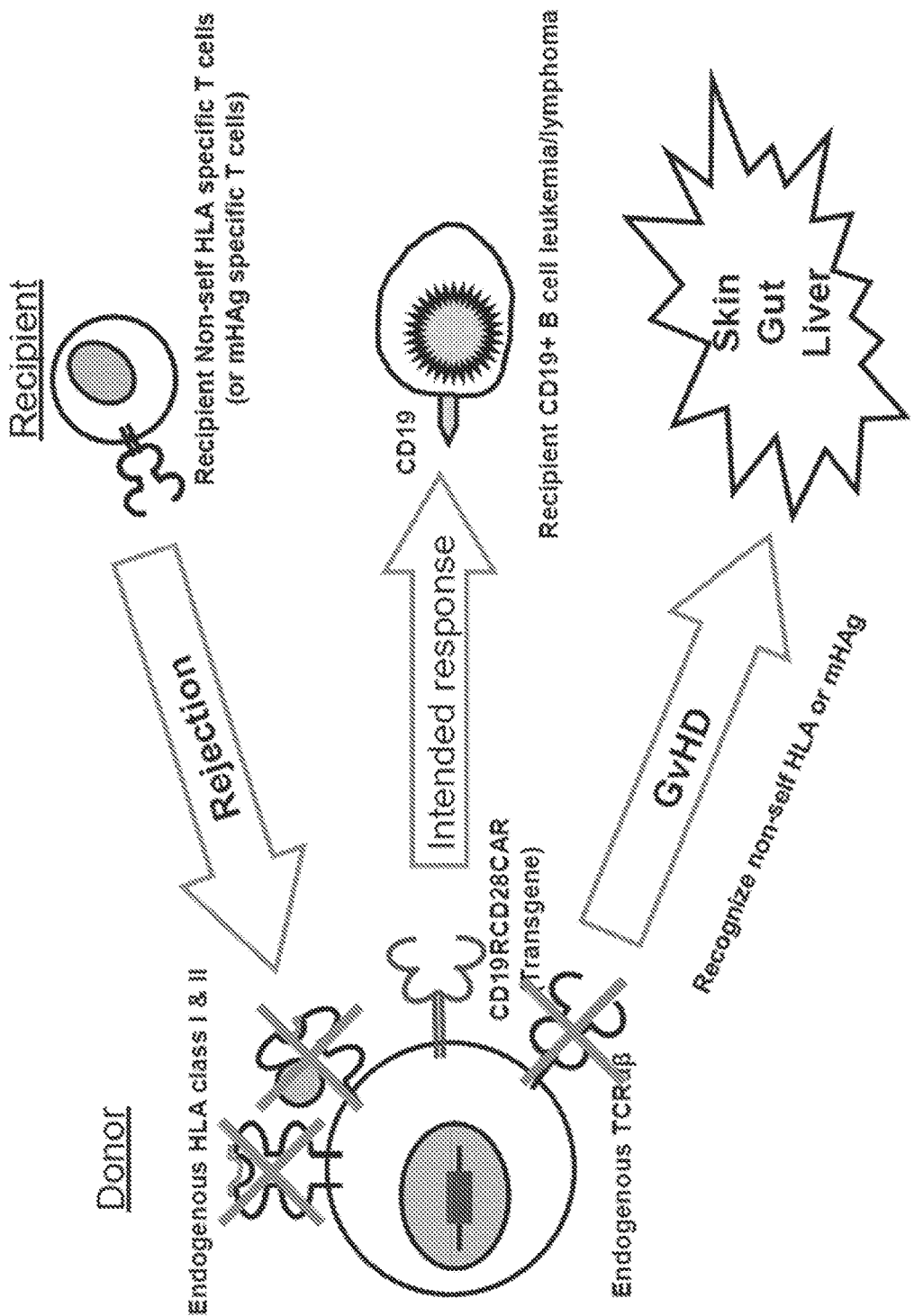

FIG. 10. An exemplary illustration of interactions between donor and recipient cells in normal cases and in embodiments of the invention.

Figure 11A:
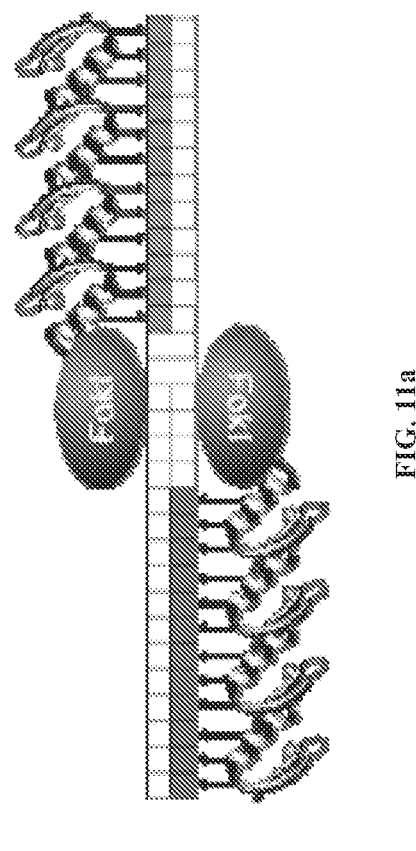
Figure 11B:
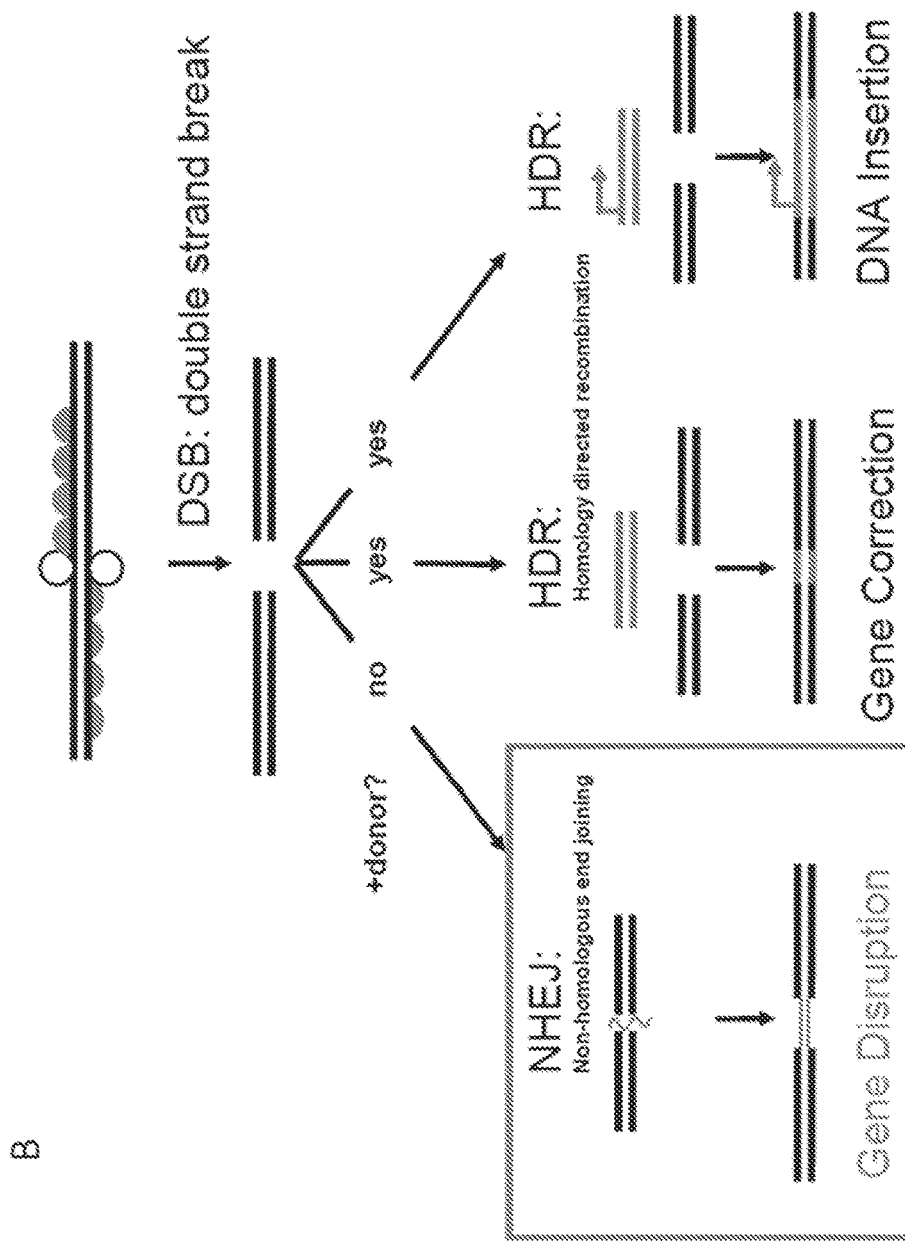

FIGS. 11a and 11b. Illustrations of use of particular zinc finger nucleases (ZFNs) to achieve elimination of HLA in the genome.

Figure 12A:
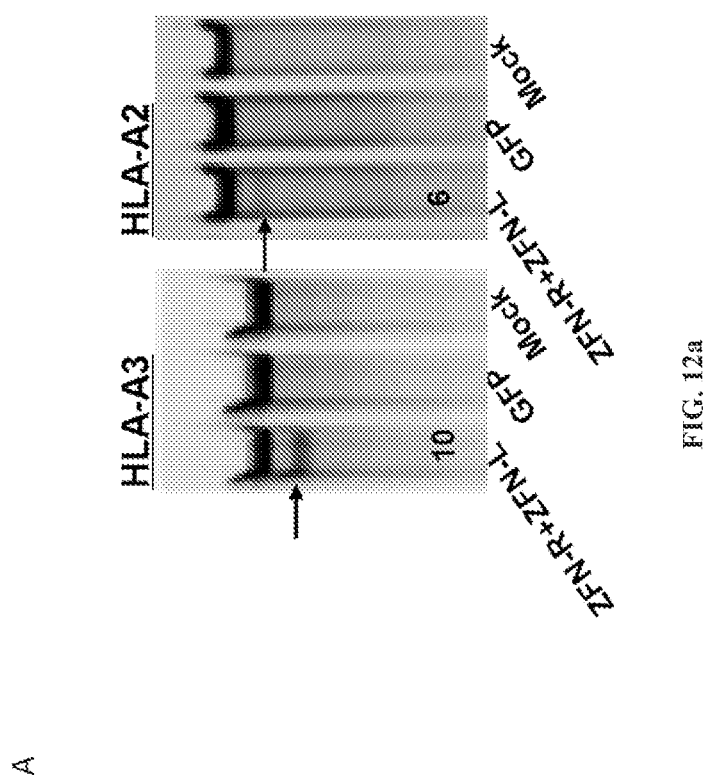
Figure 12B:
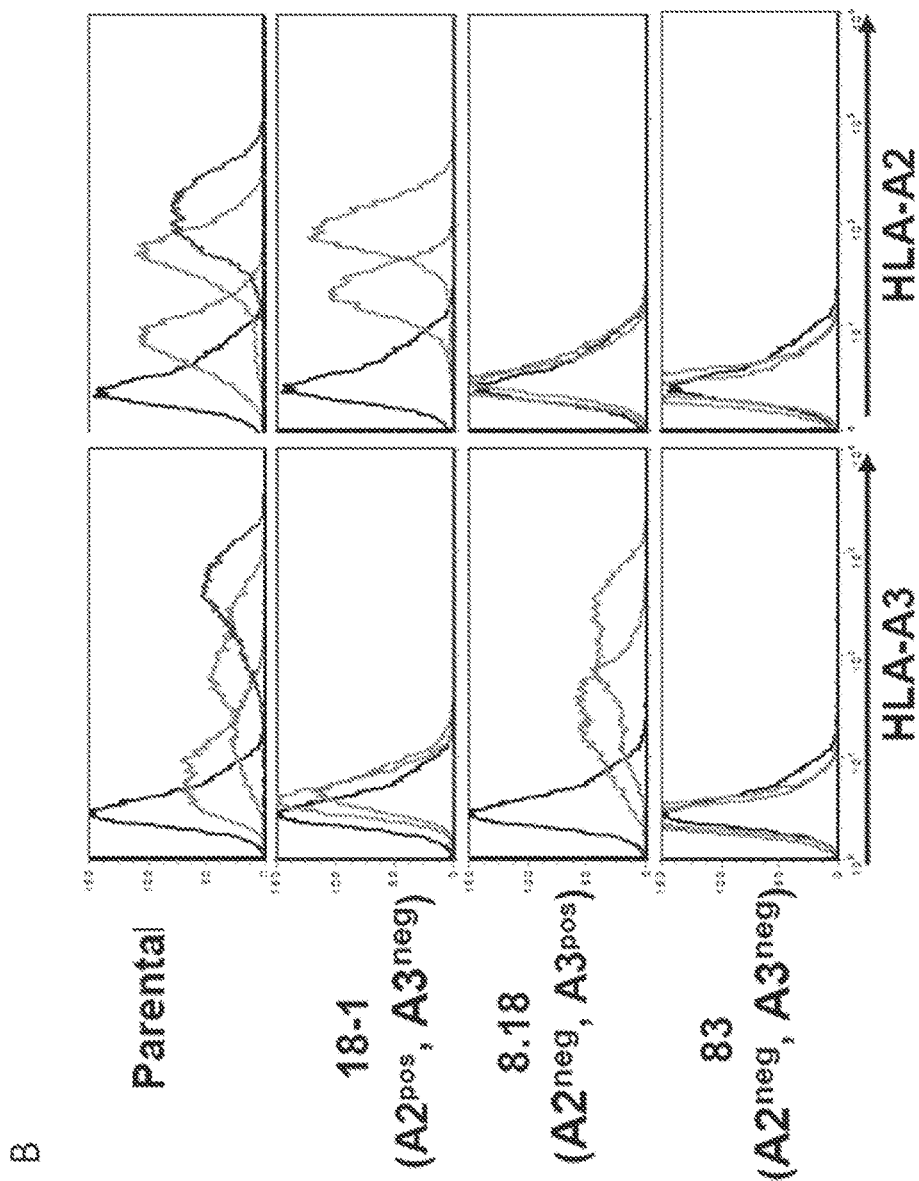
Figure 12C:
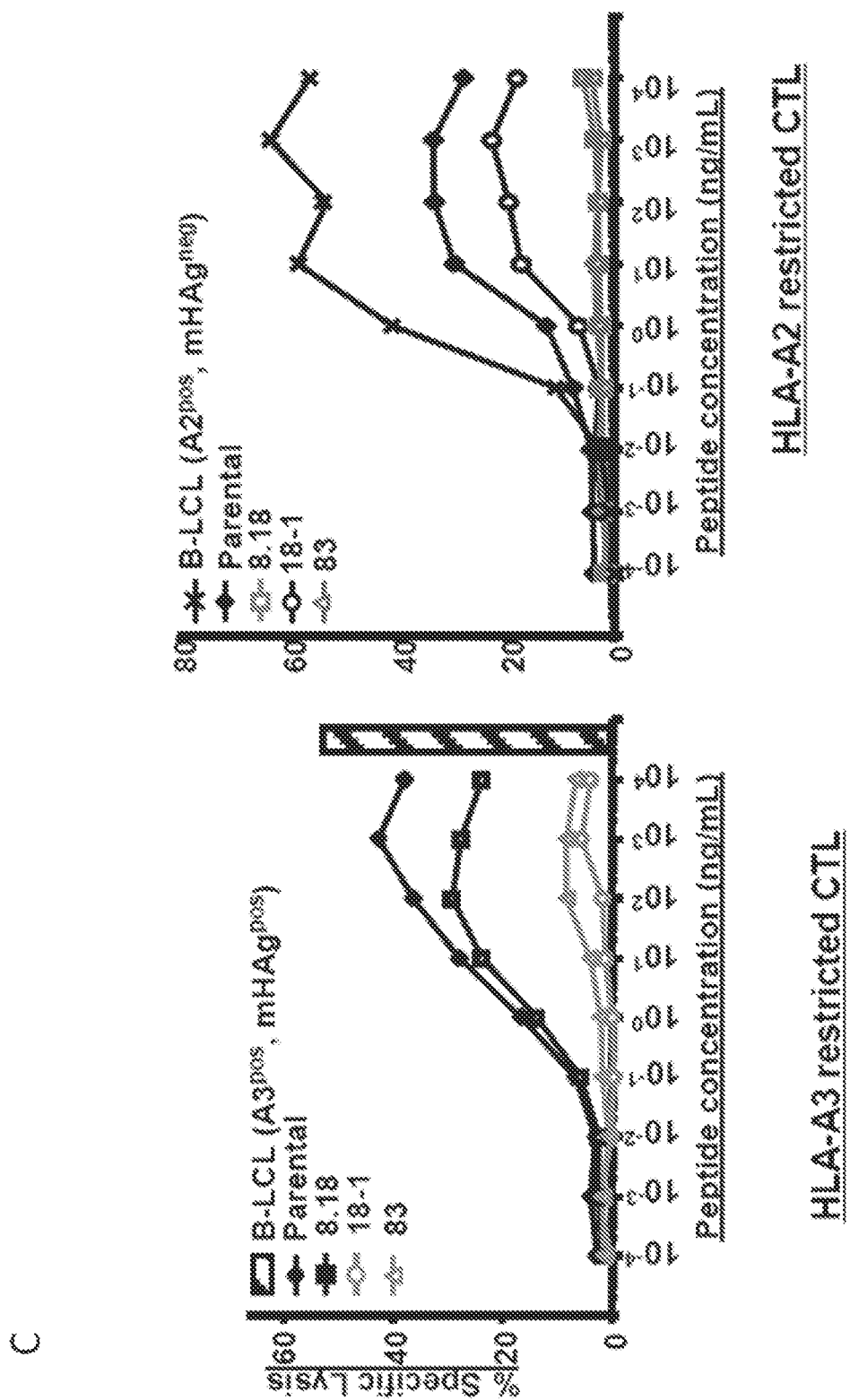

FIGS. 12a, 12b, and 12c. HLA-A targeted ZFNs are able to disrupt the HLA-A locus in HEK293 cells (FIG. 12a) to an undetectable level (FIG. 12b) and that the HEK293 cells can evade HLA-A restricted CTL clone attack.

Figure 13A:
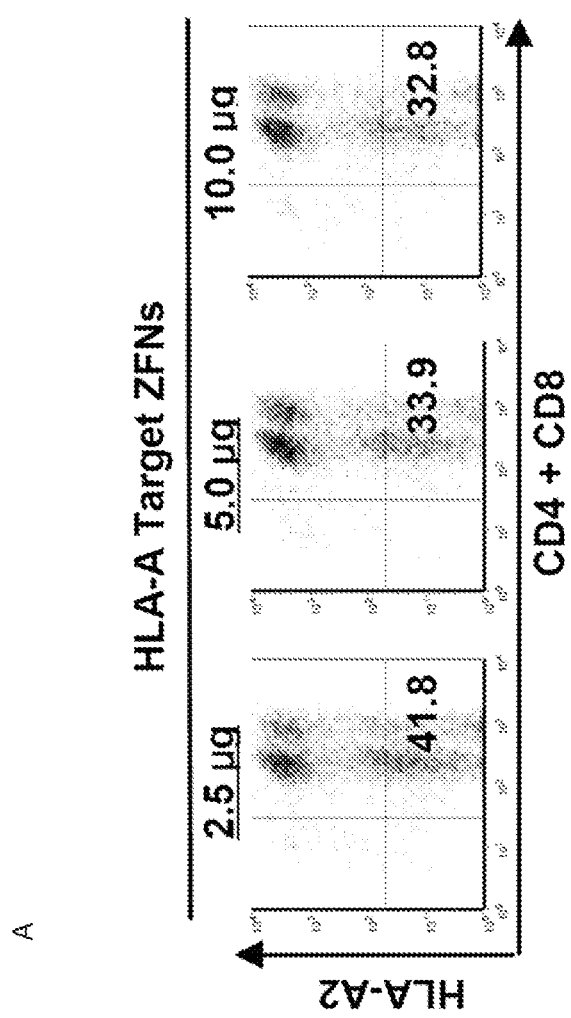
Figure 13B:
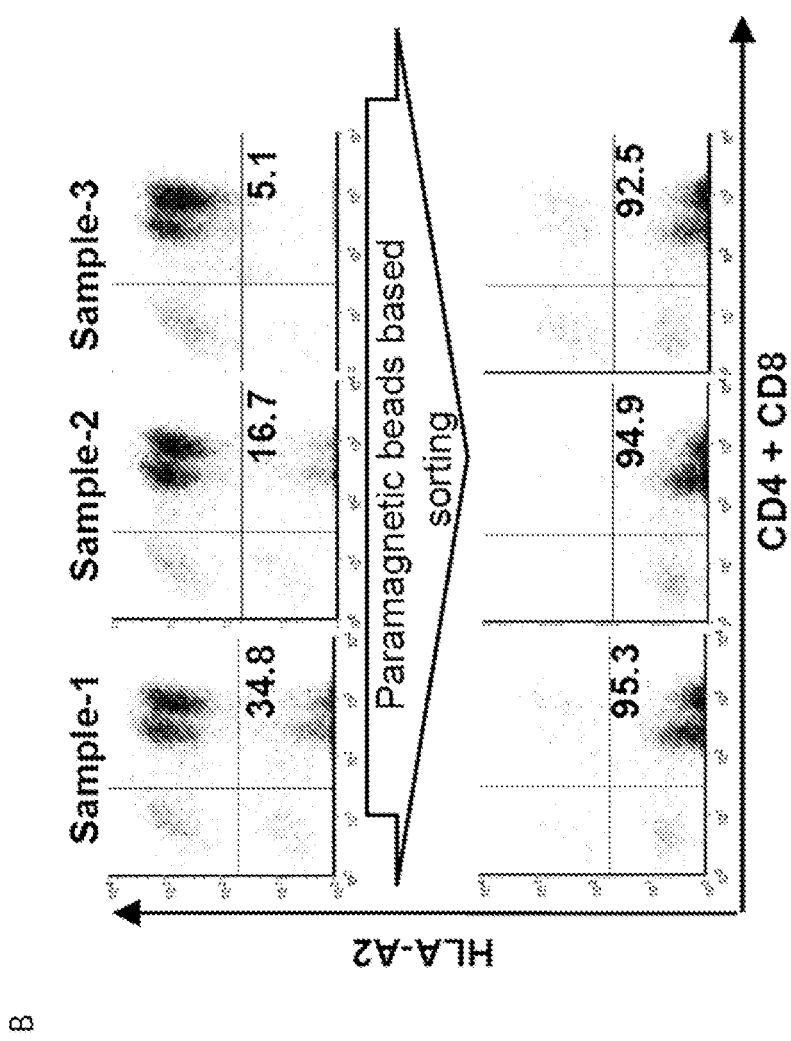

FIGS. 13a and 13b. HLA-A targeting of ZFNs disrupting HLA-A when they were expressed from in vitro transcribed mRNA (FIG. 13a). The HLA-A$^{null}$ T-cell population can be enriched (FIG. 13b).

Figure 14A:
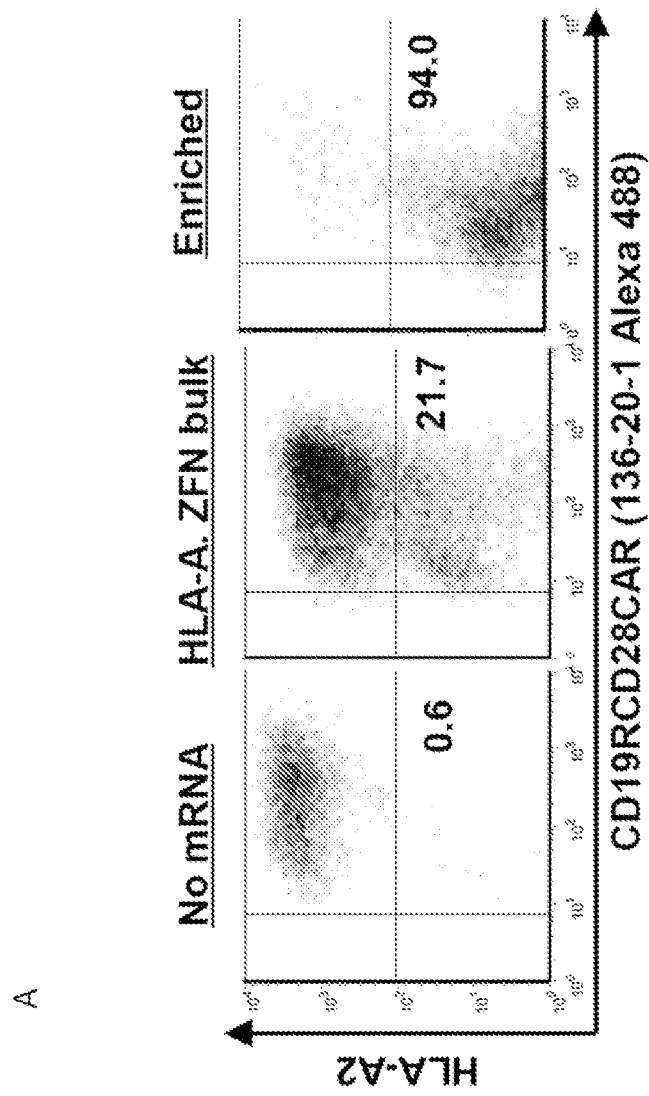
Figure 14B:
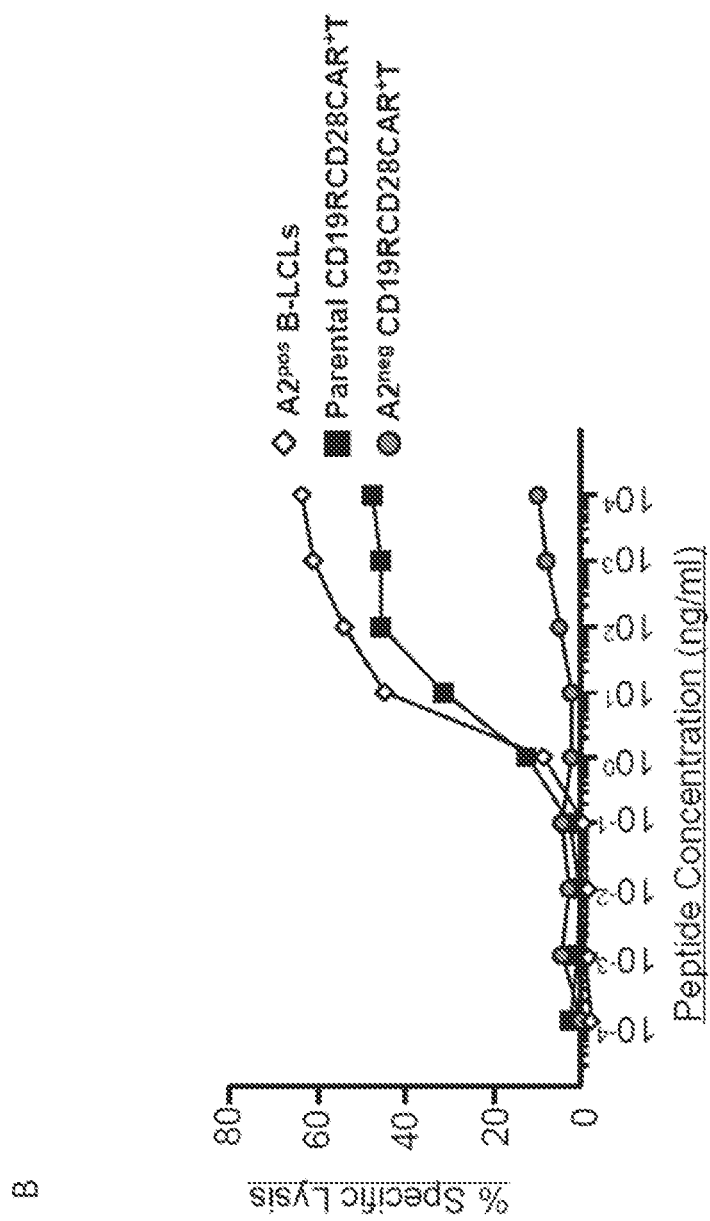
Figure 14C:
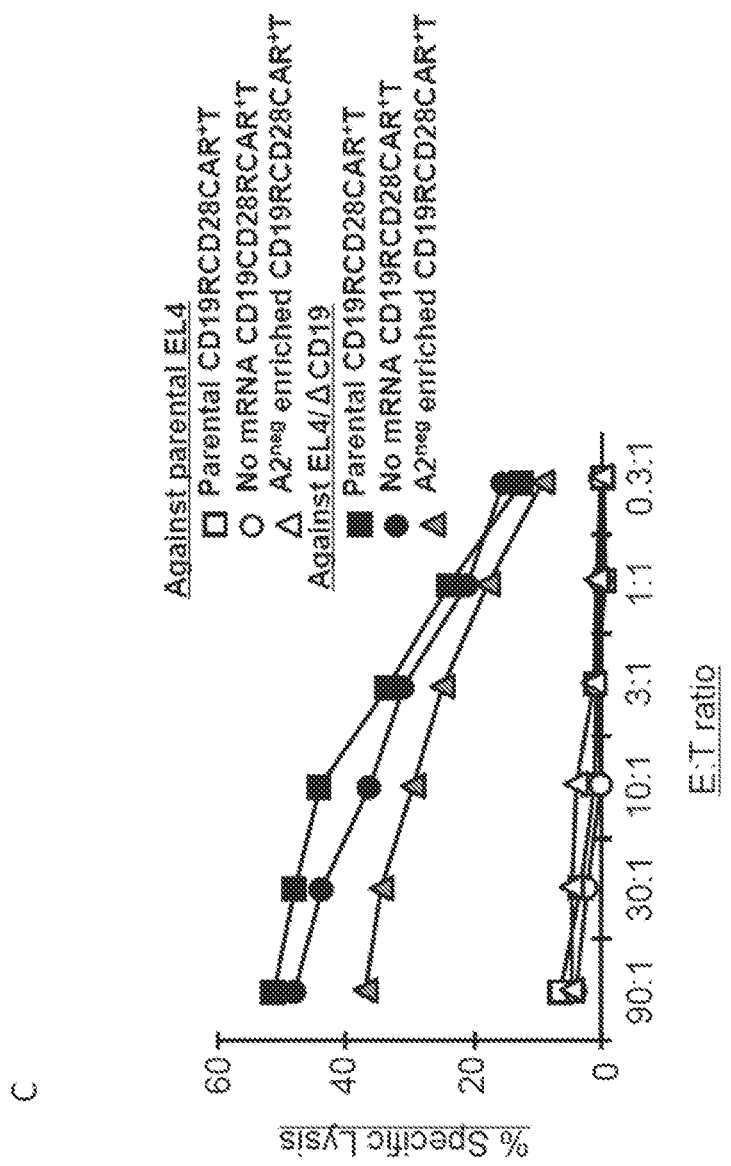

FIGS. 14a, 14b, and 14c. Disruption of HLA-A from exemplary CD19RCD28CAR$^+$ T cells (FIG. 14a) including evasion of HLA-A restricted CTL attack (FIG. 14b) but maintenance of CD19 specificity (FIG. 14c).

Figure 15A:
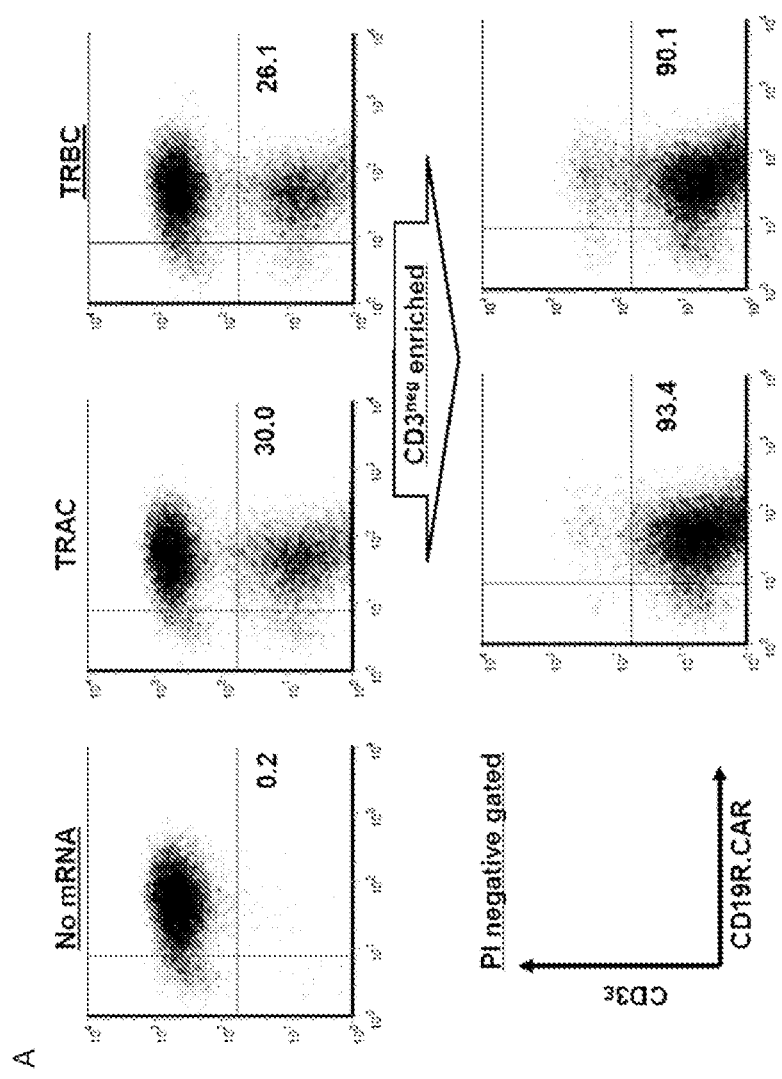
Figure 15B:
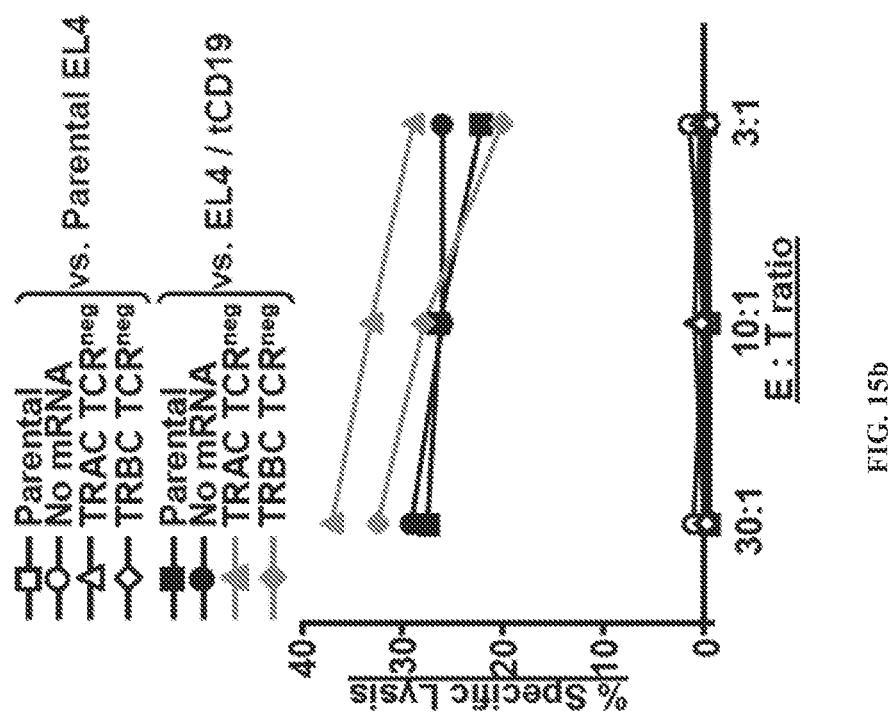
Figure 15C:
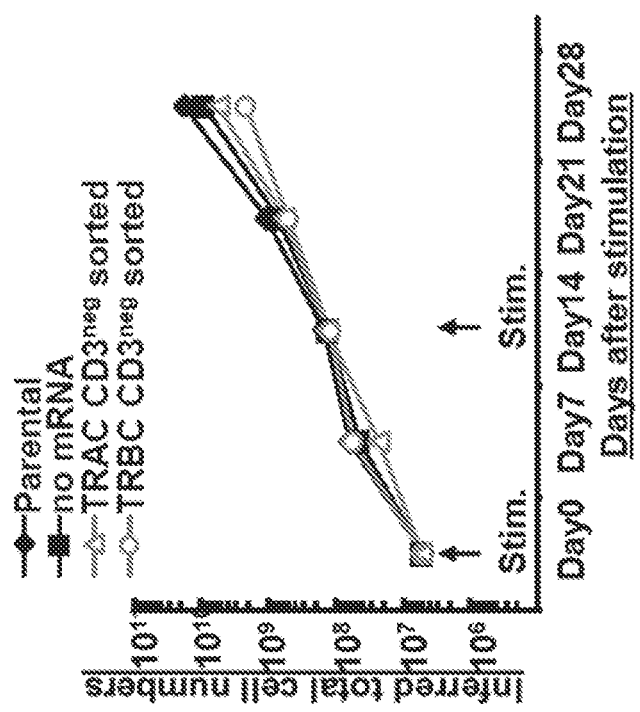

FIG. 15a. TCR expression can be disrupted from CD19RCD28CAR T cells by TCR α or β constant region-targeted ZFN pairs. FIGS. 15b and 15c. TCR$^{null}$CD19RCD28CAR$^+$ T cells maintain CD19 specific-ity (FIG. 15b) and they can be propagated on CD19-expressing K562-based artificial antigen presenting cells (FIG. 15c).

Figure 16:
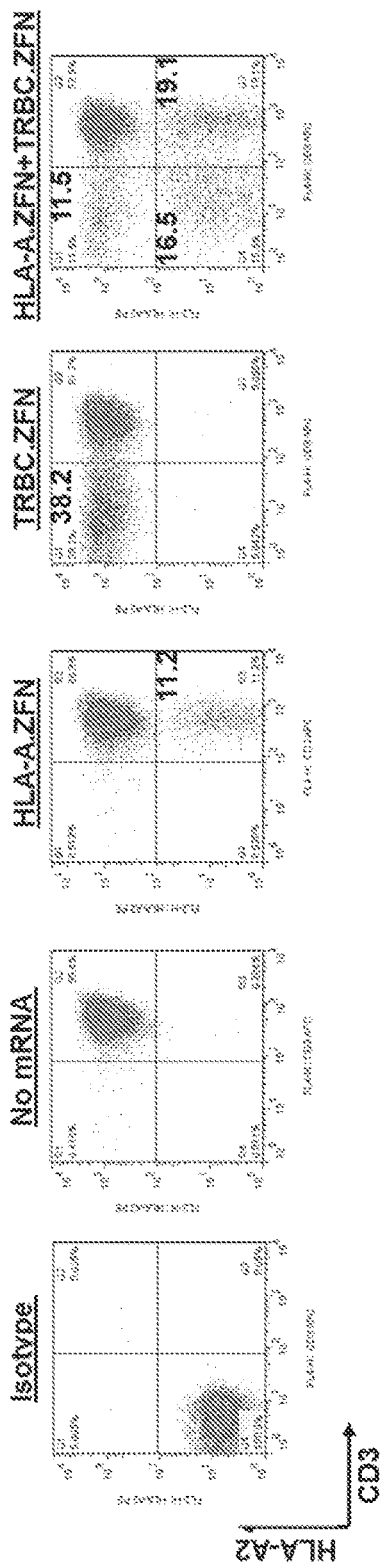

FIG. 16. Simultaneous knock out of HLA-A and TCR β. Peripheral blood mononuclear cells from HLA-A2-positive healthy donor were stimulated with OKT3 loaded artificial antigen presenting cells and cultured with 50 IU/mL of rh IL-2. Six days after stimulation, expanded T cells were electroporated with HLA-A-targeted or TCR β constant region (TRBC)-targeted ZFNs from mRNAs. Both TCR expression and HLA-A expression were evaluated by anti-CD3ε monoclonal antibody (mAb) and anti-HLA-A2 mAb four days after electroporation. PI negative cells were positively gated according to CD4 and/or CD8. Numbers in the figure represent percentage of population in each quadrant.

DESCRIPTION OF ILLUSTRATIVE EMBODIMENTS

As used herein the specification, "a" or "an" may mean one or more. As used herein in the claim(s), when used in conjunction with the word "comprising," the words "a" or "an" may mean one or more than one. As used herein "another" may mean at least a second or more. In specific embodiments, aspects of the invention may "consist essentially of" or "consist of" one or more elements or steps of the invention, for example. Some embodiments of the invention may consist of or consist essentially of one or more elements, method steps, and/or methods of the invention. It is contemplated that any method or composition described herein can be implemented with respect to any other method or composition described herein.

I. Definitions

The term "chimeric antigen receptors (CARs)" as used herein may be referred to as artificial T-cell receptors, chimeric T-cell receptors, or chimeric immunoreceptors, for example, and encompass engineered receptors that graft an artificial specificity onto a particular immune effector cell. The CARs may be employed to impart the specificity of a monoclonal antibody onto a T cell, thereby allowing a large number of specific T cells to be generated, for example, in use for adoptive cell therapy. In specific embodiments, the CARs direct specificity of the cell to a tumor associated antigen, for example. In some embodiments, the CARs comprise an intracellular activation domain, a transmembrane domain and an extracellular domain comprising a tumor associated antigen binding region. In particular aspects, CARs comprise fusions of single-chain variable fragments (scFv) derived from monoclonal antibodies, fused to CD3-zeta transmembrane and endodomain. The specificity of other CARs designs may be derived from ligands of receptors (e.g., peptides) or from Dectins. In particular embodiments, one can target malignant B cells by redirecting the specificity of T cells using a chimeric immunoreceptor specific for the B-lineage molecule, CD19. In certain cases, the CARs comprise domains for additional co-stimulatory signaling, such as CD3-zeta, FcR, CD27, CD28, CD137, DAP10, and/or OX40. In some cases molecules can be co-expressed with the CAR. These include co-stimulatory molecules, reporter genes for imaging (e.g., for positron emission tomography), gene products that conditionally ablate the T cells upon addition of a pro-drug, homing receptors, cytokines, and cytokine receptors.

The term "T-cell receptor (TCR)" as used herein refers to a protein receptor on T cells that is composed of a heterodimer of an alpha (α) and beta (β) chain, although in some cells the TCR consists of gamma and delta (γ/δ) chains. In embodiments of the invention, the TCR may be modified on any cell comprising a TCR, including a helper T cell, a cytotoxic T cell, a memory T cell, regulatory T cell, natural killer T cell, and gamma delta T cell, for example.

II. General Embodiments of the Invention

Chimeric antigen receptors (CARs) are designed for adoptive immunotherapy by connecting an extracellular antigen-binding domain to a transmembrane domain and an intracellular signaling domain (endodomain). It is a useful anti-tumor approach to eradicate tumor cells by adoptive transfer of T cells expressing chimeric antigen receptors to recognize specific antigens presented on tumor cells and activate T cells to specifically lyse these tumor cells. A critical aspect of this CAR strategy is the selection of target epitopes that are specifically or selectively expressed on tumors, are present on all tumor cells, and are membrane epitopes not prone to shed or modulate from the cell surface. However, ideally the $CAR^+$ T cells would be able to be used as a universal reagent or drug suitable for any mammalian (such as human) recipient. To employ the cells in such a manner, one must prevent their rejection in a graft-versus-host response without compromising CAR-dependent effector functions.

In embodiments of this invention, T-cell receptor (TCR) αβ disruption from chimeric antigen receptor (CAR)-expressing T cells ($CAR^+$ T cells) to establish "universal" T cell-based immunotherapy is provided. Redirecting T-cell specificity to desired antigen can be achieved through CAR. However, ex vivo generation of $CAR^+$ T cells from patient is limited by time and expense. Moreover, T cells derived from patients are sometimes functionally flawed because of the multiple rounds of lymphotoxic (lymphodepleting) chemotherapy. To this end, embodiments of the present invention concern the generation of $CAR^+$ T cells from healthy volunteer donor that can serve as "off-the-shelf" reagents. In other words, genetically modified T cells from one donor can be pre-prepared and then infused into multiple recipients. This will facilitate "centralized" manufacturing of the universal T cells and subsequent pre-positioning of the T cells at regional facilities for infusion on demand, enable clinical trials to be undertaken that are powered for efficacy, and facilitate combination therapies in which the universal T cells can be administered with other biologics and therapeutics. To achieve this, one can eliminate endogenous TCR αβ and γδ expression, which causes unwanted allogeneic immune reaction. Such steps can occur by any suitable manner, including by introducing zinc finger nucleases (ZFN), for example, targeting TCR α constant region or β constant region. Single ZFN transfection from in vitro transcribed mRNA generates up to 40% TCR αβ disrupted $CAR^+$ T cells and the $TCR\alpha\beta^{neg}$ population is readily enriched by clinically compatible paramagnetic beads based sorting. The $CAR^+TCR^{neg}$ T cells can be propagated to clinically-appealing numbers by recursive additions of irradiated artificial antigen presenting cells (aAPC). Importantly $TCR\alpha\beta^{neg}$ $CAR^+$ T cells actually do not respond to TCR αβ-CD3 stimulation while preserving target antigen specific function and proliferation through CAR. Embodiments of the invention are unique as they combine (i) redirecting the specificity of T cells by introducing a CAR and (ii) eliminating expression of endogenous TCR to generate a desired T-cell product. In certain embodiments, the introduction of CAR and elimination of TCR are accomplished by electroporation using the Sleeping Beauty (SB) system to stably express CAR and desired transient transfection of in vitro-transcribed mRNA coding for ZFNs. In embodiments of the invention, infusing specific $CAR^+TCR^{neg}$ T cells are pre-prepared from healthy donors and thawed to be infused on demand as an off-the-shelf reagent.

The inventors demonstrate that ZFNs targeting either the α or β chains of endogenous TCRs in T cells resulted in the desired loss of TCR expression. As expected, these modified T cells did not respond to TCR stimulation, but maintained their CAR mediated re-directed specificity for the exemplary antigen, CD19.

In certain embodiments of the invention, clinical-grade T-cells are genetically modified ex vivo to express a chimeric antigen receptor (CAR) to redirect specificity to a tumor associated antigen (TAA) thereby conferring anti-tumor activity in vivo. T cells expressing a CD19-specific CAR recognize B-cell malignancies in multiple recipients independent of MHC because the specificity domains are cloned from the variable chains of a CD19 monoclonal antibody. The present invention encompasses a major step towards eliminating the need to generate patient-specific T cells by generating "universal" allogeneic TAA-specific T cells from one donor that might be administered to multiple recipients. This was achieved by genetically editing CD19-specific $CAR^+$ T cells to eliminate expression of the endogenous αβ T-cell receptor (TCR) to prevent a graft-versus-host response without compromising CAR-dependent effector functions. Genetically modified T cells were generated using the Sleeping Beauty system to stably introduce the CD19-specific CAR with subsequent permanent deletion of α or β TCR chains with designer zinc finger nucleases. The inventors show that these engineered T cells display the expected property of having redirected specificity for CD19 without responding to TCR stimulation. These $CAR^+TCR^{neg}$ T cells may be used as off-the-shelf therapy for investigational treatment of B-lineage malignancies.

In particular, to test the feasibility of using allogeneic $CAR^+$ T cells the inventors modified the culturing process for generating $CAR^+$ T cells (FIG. 7) to include the editing of the genome of CAR and $CAR^+$ T cells to irreversibly eliminate expression of the αβ TCR. To knockout the αβ TCR loci the inventors developed zinc finger nucleases (ZFNs) (Urnov et al., 2010), comprised of zinc finger protein DNA-binding domains fused to the DNA cleavage domain from the FokI endonuclease, targeting genomic sequences in the constant regions of the endogenous α or β subunits of the TCR. ZFNs mediate genome editing by catalyzing the formation of a DNA double strand break (DSB) in the genome. Targeting a DSB to a predetermined site within the coding sequence of a gene has been previously shown to lead to permanent loss of functional target gene expression via repair by non-homologous end joining (NHEJ), an error-prone cellular repair pathway that results in the insertion or deletion of nucleotides at the cleaved site (Santiago et al., 2008; Perez et al., 2008).

III. Chimeric Antigen Receptors

As used herein, the term "antigen" is a molecule capable of being bound by an antibody or T-cell receptor. An antigen is additionally capable of inducing a humoral immune response and/or cellular immune response leading to the production of B and/or T lymphocytes.

The present invention involves nucleic acids, including nucleic acids encoding an antigen-specific chimeric antigen receptor (CAR), including a CAR that has been humanized to reduce immunogenicity (hCAR), polypeptide comprising an intracellular signaling domain, a transmembrane domain, and an extracellular domain comprising one or more signaling motifs. In certain embodiments, the CAR may recognize an epitope comprised of the shared space between one or more antigens. In certain embodiments, the binding region can comprise complementary determining regions of a monoclonal antibody, variable regions of a monoclonal antibody, and/or antigen binding fragment thereof. In other embodiment, that specificity is derived from a peptide (e.g., cytokine) that binds to a receptor. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor contains three CDRs (CDR1, CDR2, and CDR3). Since the antigen receptors are typically composed of two polypeptide chains, there are six CDRs for each antigen receptor that can come into contact with the antigen—each heavy and light chain contains three CDRs. Because most sequence variation associated with immunoglobulins and T-cell receptors are found in the CDRs, these regions are sometimes referred to as hypervariable domains. Among these, CDR3 shows the greatest variability as it is encoded by a recombination of the VJ (VDJ in the case of heavy chain and TCR αβ chain) regions.

It is contemplated that the human CAR nucleic acids are human genes to enhance cellular immunotherapy for human patients.

In a specific embodiment, the invention includes a full length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into what has been referred to by Winters as a diabody. The hinge portion of the construct can have multiple alternatives from being totally deleted, to having the first cysteine maintained, to a proline rather than a serine substitution, to being truncated up to the first cysteine. The Fc portion can be deleted, although there is data to suggest that the receptor preferably extends from the membrane. Any protein that is stable and dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization.

The intracellular signaling domain of the chimeric receptor of the invention is responsible for activation of at least one of the normal effector functions of the immune cell in which the chimeric receptor has been placed. The term "effector function" refers to a specialized function of a differentiated cell. Effector function of a T cell, for example, may be cytolytic activity or helper activity including the secretion of cytokines. Effector function in a memory or memory-type T cell includes antigen-dependent proliferation. Thus the term "intracellular signaling domain" refers to the portion of a protein that transduces the effector function signal and directs the cell to perform a specialized function. While usually the entire intracellular signaling domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term intracellular signaling domain is thus meant to include any truncated portion of the intracellular signaling domain sufficient to transduce the effector function signal. Examples include the zeta chain of the T-cell receptor or any of its homologs (e.g., eta, delta, gamma, or epsilon). MB1 chain, B29, Fc RIII, Fc RI, and combinations of signaling molecules, such as CD3ζ and CD28, 4-1BB, OX40, and combination thereof, as well as other similar molecules and fragments. Intracellular signaling portions of other members of the families of activating proteins can be used, such as FcγRIII and FcεRI. See Gross et al. (1992). Stancovski et al. (1993), Moritz et al. (1994), Hwu et al. (1995), Weijtens et al. (1996), and Hekele et al. (1996) for disclosures of cTCR's using these alternative transmembrane and intracellular domains. In a preferred embodiment, the human CD3 ζ intracellular domain was taken for activation.

The antigen-specific extracellular domain and the intracellular signaling-domain may be linked by a transmembrane domain, such as the human $IgG_4Fc$ hinge and Fc regions. Alternatives include the human CD4 transmembrane domain, the human CD28 transmembrane domain, the transmembrane human CD3ζ domain, or a cysteine mutated human CD3ζ domain, or other transmembrane domains from other human transmembrane signaling proteins, such as CD16 and CD8 and erythropoietin receptor.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, OX-40 (CD134), DAP10, and 4-1BB (CD137). In addition to a primary signal initiated by CD3 ζ, an additional signal provided by a human costimulatory receptor inserted in a human CAR is important for full activation of T cells and could help improve in vivo persistence and the therapeutic success of the adoptive immunotherapy.

In particular embodiments, the invention concerns isolated nucleic acid segments and expression cassettes incorporating DNA sequences that encode the CAR. Vectors of the present invention are designed, primarily, to deliver desired genes to immune cells, preferably T cells under the control of regulated eukaryotic promoters, for example, MNDU3 promoter or EF1apha promoter, or Ubiquitin promoter. Also, the vectors may contain a selectable marker if, for no other reason, to facilitate their manipulation in vitro.

Chimeric antigen receptor molecules are recombinant and are distinguished by their ability to both bind antigen and transduce activation signals via immunoreceptor activation motifs (ITAM's) present in their cytoplasmic tails. Receptor constructs utilizing an antigen-binding moiety (for example, generated from single chain antibodies (scFv)) afford the additional advantage of being "universal" in that they bind native antigen on the target cell surface in an HLA-independent fashion. For example, several laboratories have reported on scFv constructs fused to sequences coding for the intracellular portion of the CD3 complex's zeta chain (ζ), the Fc receptor gamma chain, and sky tyrosine kinase (Eshhar et al., 1993; Fitzer-Attas et al., 1998). Re-directed T cell effector mechanisms including tumor recognition and lysis by CTL have been documented in several murine and human antigen-scFv: ζ systems (Eshhar, 1997; Altenschmidt et al., 1997; Brocker et al., 1998).

To date non-human antigen binding regions are typically used in constructing a chimeric antigen receptor. A potential problem with using non-human antigen binding regions, such as murine monoclonal antibodies, is the lack of human effector functionality and inability to penetrate into tumor masses. In other words, such antibodies may be unable to mediate complement-dependent lysis or lyse human target cells through antibody-dependent cellular toxicity or Fc-receptor mediated phagocytosis to destroy cells expressing CAR. Furthermore, non-human monoclonal antibodies can be recognized by the human host as a foreign protein, and therefore, repeated injections of such foreign antibodies can lead to the induction of immune responses leading to harmful hypersensitivity reactions. For murine-based monoclonal antibodies, this is often referred to as a Human Anti-Mouse Antibody (HAMA) response. Therefore, the use of human antibodies is more preferred because they do not elicit as strong a HAMA response as murine antibodies. Similarly, the use of human sequences in the CAR can avoid immune-mediated recognition and therefore elimination by endogenous T cells that reside in the recipient and recognize processed antigen in the context of HLA.

In some embodiments, the chimeric antigen receptor comprises: a) an intracellular signaling domain, b) a transmembrane domain, and c) an extracellular domain comprising an antigen binding region.

In specific embodiments, intracellular receptor signaling domains in the CAR include those of the T cell antigen receptor complex, such as the zeta chain of CD3, also Fcγ RIII costimulatory signaling domains, CD28, DAP10, CD2, alone or in a series with CD3zeta, for example. In specific embodiments, the intracellular domain (which may be referred to as the cytoplasmic domain) comprises part or all of one or more of TCR zeta chain, CD28, OX40/CD134, 4-1BB/CD137, FcεRIγ, ICOS/CD278, ILRB/CD122, IL-2RG/CD132, DAP molecule, CD27, DAP10, DAP12, and CD40. In some embodiments, one employs any part of the endogenous T cell receptor complex in the intracellular domain. One or multiple cytoplasmic domains may be employed, as so-called third generation CARs have at least two or three signaling domains fused together for additive or synergistic effect, for example.

In certain embodiments of the chimeric antigen receptor, the antigen-specific portion of the receptor (which may be referred to as an extracellular domain comprising an antigen binding region) comprises a tumor associated antigen or a pathogen-specific antigen.

A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, epithelial tumor antigen, melanoma-associated antigen, mutated p53, mutated ras, and so forth.

In certain embodiments intracellular tumor associated antigens may be targeted, such as HA-1, surviving, WT1, p53. This can be achieved by a CAR expressed on a universal T cell that recognizes the processed peptide described from the intracellular tumor associated antigen in the context of HLA. In addition, the universal T cell may be genetically modified to express a T-cell receptor pairing that recognizes the intracellular processed tumor associated antigen in the context of HLA.

The pathogen may be of any kind, but in specific embodiments the pathogen is a fungus, bacteria, or virus, for example. Exemplary viral pathogens include those of the families of Adenoviridae, Epstein-Barr virus (EBV). Cytomegalovirus (CMV), Respiratory Syncytial Virus (RSV), JC virus, BK virus, HSV, HHV family of viruses, Picornaviridae, Herpesviridae, Hepadnaviridae, Flaviviridae, Retroviridae, Orthomyxoviridae. Paramyxoviridae, Papovaviridae, Polyomavirus, Rhabdoviridac, and Togaviridae. Exemplary pathogenic viruses cause smallpox, influenza, mumps, measles, chickenpox, ebola, and rubella. Exemplary pathogenic fungi include *Candida, Aspergillus, Cryptococcus, Histoplasma, Pneumocystis,* and *Stachvbotrys*. Exemplary pathogenic bacteria include *Streptococcus. Pseudomonas, Shigella, Campylobacter, Staphylococcus, Helicobacter, E. coli, Rickettsia, Bacillus, Bordetella, Chlamydia, Spirochetes,* and *Salmonella*. In one embodiment the pathogen receptor Dectin-1 can be used to generate a CAR that recognizes the carbohydrate structure on the cell wall of fungi. T cells genetically modified to express the CAR based on the specificity of Dectin-1 can recognize *Aspergillus* and target hyphal growth. In another embodiment, CARs can be made based on an antibody recognizing viral determinants (e.g., the glycoproteins from CMV and Ebola) to interrupt viral infections and pathology.

In some embodiments, the pathogenic antigen is an *Aspergillus* carbohydrate antigen for which the extracellular domain in the CAR recognizes patterns of carbohydrates of the fungal cell wall.

A chimeric immunoreceptor according to the present invention can be produced by any means known in the art, though preferably it is produced using recombinant DNA techniques. A nucleic acid sequence encoding the several regions of the chimeric receptor can be prepared and assembled into a complete coding sequence by standard techniques of molecular cloning (genomic library screening, PCR, primer-assisted ligation, scFv libraries from yeast and bacteria, site-directed mutagenesis, etc.). The resulting coding region can be inserted into an expression vector and used to transform a suitable expression host allogeneic TCR$^{neg}$ cell line.

As used herein, a nucleic acid construct or nucleic acid sequence or polynucleotide is intended to mean a DNA molecule that can be transformed or introduced into a T cell and be transcribed and translated to produce a product (e.g., a chimeric receptor).

In an exemplary nucleic acid construct (polynucleotide) employed in the present invention, the promoter is operably linked to the nucleic acid sequence encoding the chimeric receptor of the present invention, i.e., they are positioned so as to promote transcription of the messenger RNA from the DNA encoding the chimeric receptor. The promoter can be of genomic origin or synthetically generated. A variety of promoters for use in T cells are well-known in the art (e.g., the CD4 promoter disclosed by Marodon et al. (2003)). The promoter can be constitutive or inducible, where induction is associated with the specific cell type or a specific level of maturation, for example. Alternatively, a number of well-known viral promoters are also suitable. Promoters of interest include the (i-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel and Goldfeld, 2003). Also, it may be further advantageous to use endogenous or exogenous non-coding regions to stabilize the mRNA.

For expression of a chimeric receptor of the present invention, the naturally occurring or endogenous transcriptional initiation region of the nucleic acid sequence encoding N-terminal components of the chimeric receptor can be used to generate the chimeric receptor in the target host. Alternatively, an exogenous transcriptional initiation region can be used that allows for constitutive or inducible expression, wherein expression can be controlled depending upon the target host, the level of expression desired, the nature of the target host, and the like.

Likewise, a signal sequence directing the chimeric receptor to the surface membrane can be the endogenous signal sequence of N-terminal component of the chimeric receptor. Optionally, in some instances, it may be desirable to exchange this sequence for a different signal sequence. However, the signal sequence selected should be compatible with the secretory pathway of T cells so that the chimeric receptor is presented on the surface of the T cell.

Similarly, a termination region may be provided by the naturally occurring or endogenous transcriptional termination region of the nucleic acid sequence encoding the C-terminal component of the chimeric receptor. Alternatively, the termination region may be derived from a different source. For the most part, the source of the termination region is generally not considered to be critical to the expression of a recombinant protein and a wide variety of termination regions can be employed without adversely affecting expression.

As will be appreciated by one of skill in the art that, in some instances, a few amino acids at the ends of the antigen binding domain in the CAR can be deleted, usually not more than 10, more usually not more than 5 residues, for example. Also, it may be desirable to introduce a small number of amino acids at the borders, usually not more than 10, more usually not more than 5 residues. The deletion or insertion of amino acids may be as a result of the needs of the construction, providing for convenient restriction sites, ease of manipulation, improvement in levels of expression, or the like. In addition, the substitute of one or more amino acids with a different amino acid can occur for similar reasons, usually not substituting more than about five amino acids in any one domain.

The chimeric construct that encodes the chimeric receptor according to the invention can be prepared in conventional ways. Because, for the most part, natural sequences may be employed, the natural genes may be isolated and manipulated, as appropriate, so as to allow for the proper joining of the various components. Thus, the nucleic acid sequences encoding for the N-terminal and C-terminal proteins of the chimeric receptor can be isolated by employing the polymerase chain reaction (PCR), using appropriate primers that result in deletion of the undesired portions of the gene. Alternatively, restriction digests of cloned genes can be used to generate the chimeric construct. In either case, the sequences can be selected to provide for restriction sites that are blunt-ended, or have complementary overlaps.

The various manipulations for preparing the chimeric construct can be carried out in vitro and in particular embodiments the chimeric construct is introduced into vectors for cloning and expression in an appropriate host using standard transformation or transfection methods. Thus, after each manipulation, the resulting construct from joining of the DNA sequences is cloned, the vector isolated, and the sequence screened to ensure that the sequence encodes the desired chimeric receptor. The sequence can be screened by restriction analysis, sequencing, or the like.

The chimeric constructs of the present invention find application in subjects having or suspected of having cancer by reducing the size of a tumor or preventing the growth or re-growth of a tumor in these subjects. Accordingly, the present invention further relates to a method for reducing growth or preventing tumor formation in a subject by introducing a chimeric construct of the present invention into an isolated T cell of the subject and reintroducing into the subject the transformed T cell, thereby effecting anti-tumor responses to reduce or eliminate tumors in the subject. Suitable T cells that can be used include cytotoxic lymphocytes (CTL) or any cell having a T cell receptor in need of disruption. As is well-known to one of skill in the art, various methods are readily available for isolating these cells from a subject. For example, using cell surface marker expression or using commercially available kits (e.g., ISO-CELL™ from Pierce, Rockford, Ill.).

It is contemplated that the chimeric construct can be introduced into the subject's own T cells as naked DNA or in a suitable vector. Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention.

Alternatively, a viral vector (e.g., a retroviral vector, adenoviral vector, adeno-associated viral vector, or lentiviral vector) can be used to introduce the chimeric construct into T cells. Suitable vectors for use in accordance with the method of the present invention are non-replicating in the subject's T cells. A large number of vectors are known that are based on viruses, where the copy number of the virus maintained in the cell is low enough to maintain the viability of the cell. Illustrative vectors include the pFB-neo vectors (STRATAGENE®) disclosed herein as well as vectors based on HIV, SV40, EBV. HSV, or BPV.

Once it is established that the transfected or transduced T cell is capable of expressing the chimeric receptor as a surface membrane protein with the desired regulation and at a desired level, it can be determined whether the chimeric receptor is functional in the host cell to provide for the desired signal induction. Subsequently, the transduced T cells are reintroduced or administered to the subject to activate anti-tumor responses in the subject. To facilitate administration, the transduced T cells according to the invention can be made into a pharmaceutical composition or made into an implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed that does not ineffectuate the cells expressing the chimeric receptor. Thus, desirably the transduced T cells can be made into a pharmaceutical composition containing a balanced salt solution, preferably Hanks' balanced salt solution, or normal saline.

IV. Exemplary Human CD19-Specific Chimeric T-Cell Receptor (or Chimeric Antigen Receptor, CAR)

CD19, a cell surface glycoprotein of the immunoglobulin superfamily, is a potentially attractive target for antibody therapy of B cell-associated malignancies. This antigen is absent from hematopoietic stem cells, and in healthy individuals its presence is exclusively restricted to the B-lineage and possibly some follicular dendritic cells (Scheuermann et al., 1995). In fact, it is present on B cells from the earliest recognizable B-lineage cells during development to B-cell blasts but is lost on maturation to plasma cells. Furthermore, CD19 is not shed from the cell surface and rarely lost during neoplastic transformation (Scheuermann et al., 1995). The protein is expressed on most malignant B-lineage cells, including cells from patients with chronic lymphocytic leukemia (CLL), non-Hodgkin lymphoma (NHL), and acute lymphoblastic leukemia (ALL) (Uckun et al., 1988). CD19 primarily acts as a B cell co-receptor in conjunction with CD21 and CD81. Upon activation, the cytoplasmic tail of CD19 becomes phosphorylated, which leads to binding by Src-family kinases and recruitment of PI-3 kinase.

In one aspect compositions of the invention include a human CD19-specific chimeric T cell receptor (or chimeric antigen receptor, CAR) polypeptide (designated hCD19CAR) comprising an intracellular signaling domain, a transmembrane domain, and an extracellular domain, the extracellular domain comprising a human CD19 binding region. In another aspect, the CD19 binding region is an F(ab')2, Fab', Fab, Fv, or scFv. The binding region may comprise an amino acid sequence that is at least, at most or about 70%, 75%, 80%, 85%, 90%, 95%, 96%, 97%, 98%, 99%, or 100% identical to the wild-type amino acid sequence. The intracellular domain may comprise an intracellular signaling domain of human CD3ζ and may further comprise human CD28 intracellular segment. In certain aspects the transmembrane domain is a CD28 transmembrane domain.

In a further aspect compositions of the invention include a nucleic acid encoding the polypeptide described above. In certain aspects the nucleic acid sequence is optimized for human codon usage.

In still a further aspect compositions of the invention include cells expressing the polypeptide described herein. The T cell may comprise an expression cassette encoding hCD19CAR polypeptide. The expression cassette can be comprised in a non-viral vector, such as a transposon, or a human transposon, or recombinant variant thereof. The expression cassette can be comprised in a viral vector or recombinant variant thereof. The expression cassette can be genomically integrated or episomally maintained or expressed from mRNA.

In yet a further aspect the invention includes a method of making a T cell expressing a human CD19-specific CAR comprising introducing an expression cassette into the cell, wherein the expression cassette encodes a polypeptide comprising a human extracellular CD19 binding domain, a transmembrane domain, and one or more intracellular signaling domain(s). The method may further comprise stimulating the cells with CD19$^+$ cells, recombinant CD19, or an antibody to the receptor to cause the cells to proliferate, kill, and/or make cytokines; for example, the cells may be stimulated to proliferate or expand with CD19$^+$ artificial antigen presenting cells.

In certain aspects the invention includes methods of treating a human disease condition associated with a TCR cell expressing endogenous CD19 comprising infusing a patient with an amount of a recombinant cell expressing a human CD19-specific CAR sufficient to treat the condition, wherein the human CD19-specific CAR comprises a human CD19 extracellular binding domain, a transmembrane domain, and an intracellular signaling domain. The condition can be lymphoma, leukemia, Non-Hodgkin's lymphoma, acute lymphoblastic leukemia, chronic lymphoblastic leukemia, chronic lymphocytic leukemia, or B cell-associated autoimmune diseases, for example.

The invention relates to the generation of a human CD19-specific chimeric antigen receptor (hCD19RCD28 or hCAR). In certain aspects recombinant cells expressing hCAR have improved in vivo persistence and anti-tumor efficacy. The human hCAR has a reduced immunogenicity compared to murine hCAR, which comprises a scFv segment derived from a murine CD19-specific monoclonal antibody (mAb). Anti-tumor effects can be augmented by genetically modified cells, such as TCR$^{neg}$ cells rendered specific for CD19. Typically, T cell specificity is achieved by electrotransfer of an expression cassette encoding hCAR.

The hCAR may be a chimeric receptor comprising one or more activation endodomain(s), such as a CD3-ζ-derived activation domain. Additional T-cell activation motifs include, but are not limited to, CD28, OX-40, and 4-1BB. In certain aspects the activation domain can also include a CD28 transmembrane and/or activation domain. In a further aspect the hCAR encoding region and/or expression cassette codon optimized for expression in human cells and subjects, e.g., in one embodiment the scFv region obtained from VH and VL sequences of a CD19-specific human antibodies are incorporated into the CD19 binding segment of the hCAR (for example see U.S. Pat. No. 7,109,304, which is incorporated herein by reference in its entirety). In another embodiment, the hCAR expression cassette is episomally maintained or integrated into the genome of the recombinant cell. In certain aspects the expression cassette is comprised in a nucleic acid capable of integration by using an integrase mechanism, a viral vector, such as a retroviral vector, or a nonviral vector, such as a transposon mechanism. In a further embodiment the expression cassette is included in a transposon based nucleic acid. In a particular embodiment, the expression cassette is part of a two component Sleeping Beauty (SB) or piggyBac system that utilizes a transposon and transposase for enhanced non-viral gene transfer.

Recombinant hCAR expressing cells can be numerically expanded to clinically-meaningful numbers. One example of such expansion uses artificial antigen presenting cells (aAPC). Recombinant hCAR expressing cells can be verified and identified by flow cytometry and western blot analyses. Recombinant hCAR expressing T cells, expressing a CD19-specific CAR can recognize and kill CD19 expressing target cells. In a further aspect, hCAR can be expressed into Universal cells that can be infused across transplantation barriers to help prevent immunogenicity. The hCAR can be used along with human genes for imaging (such as by positron emission tomography, PET) and conditional ablation of T cells, in the event of cytotoxicity. The recombinant cells of the invention can be used in CD19-specific cellular therapies.

V. Exemplary Methods and Compositions for Disrupting TCR α/β Chains

In the present invention, the T cells employed in methods and compositions lack functional T cell receptor. Although in some cases one could employ knockdown measures to impact TCR levels post-transcriptionally, such as with siRNA, in particular cases one utilizes knockout means to edit genomic DNA. In certain embodiments, one eliminates expression of the endogenous TCR. In particular embodiments, the system used to genetically modify the T cells employs stably introducing an expression construct that permits permanent deletion of α and/or β chains of TCR.

Although in some cases one could employ homologous recombination, in particular cases one utilizes non-homologous end joining to edit the genome. Any suitable protocol to modify the genome of a particular T cell is useful, although in specific embodiments one can employ zinc finger nucleases or TALE endonucleases.

In specific embodiments, one targets disruption of a and/or P chains of TCR. Although in some cases the TCR in the cell is disrupted prior to modification of the cell with a chimeric receptor, in particular cases the TCR in the cell is disrupted following modification of the cell with the chimeric receptor. The skilled artisan recognizes that this sequence of events is beneficial, given that knockout of the TCR results in loss of the ability to trigger the T cell to activate for proliferation; in the instance where the TCR is disrupted following insertion of the CAR, the cell can then propagate via the CAR.

In some embodiments, recombinant restriction enzymes called TALENs are employed that include the TAL effector DNA-binding domain fused to a DNA cleavage domain. The DNA-binding domain of the fusion protein are proteins secreted by *Xanthomonas* bacteria that comprise a highly conserved 33-34 amino acid sequence. The exception therein is at the 12th and 13th amino acids that are highly variable (Repeat Variable Diresidue) and correlate with specific nucleotide recognition in a particular code. This correlation between amino acid sequence and DNA recognition provides the generation of specific DNA binding domains by choosing a particular combination of repeat segments containing the proper RVDs, for example.

TALENs can be used to alter the genome of T cells by inducing double-strand breaks (DSB) that the T cells respond to with repair mechanisms. Non-homologous end joining (NHEJ) rejoins DNA from both sides of a double-strand break in which there is little or no sequence overlap for annealing. In the case of the present invention, this repair mechanism beneficially induces errors in the genome via insertion, deletion, or chromosomal rearrangement such that the T-cell receptor encoded thereby is non-functional.

The ability to prevent T-cell receptor expression is dependent on the ability to disrupt the endogenous expression cassette. Since a T cell can be activated by as few as one T-cell receptor molecule, efforts to disrupt T-cell receptor expression at the level of post-transcriptional (or post-translational) modification (such as using interfering RNA species) are unlikely to be completely efficient leading to leakage and expression of the endogenous T-cell receptor. Thus, the only available method to prevent T-cell receptor expression is based on genetic disruption of the alpha and/or beta expression loci as can be achieved using designer zinc finger nucleases.

VI. Methods and Compositions Related to Embodiments of the Invention

In certain aspects, the invention includes a method of making and/or expanding the antigen-specific redirected $TCR^{neg}$ cells that comprises transfecting $TCR^{neg}$ cells with an expression vector containing a DNA construct encoding the hCAR, then stimulating the cells with CD19+ cells, recombinant CD19, or an antibody to the receptor to cause the cells to proliferate.

In another aspect, this invention is a method of stably transfecting and re-directing T cells by electroporation, or other non-viral gene transfer (such as, but not limited to sonoporation) using naked DNA. Most investigators have used viral vectors to carry heterologous genes into T cells. By using naked DNA, the time required to produce redirected T cells can be reduced. "Naked DNA" means DNA encoding a chimeric T-cell receptor (cTCR) contained in an expression cassette or vector in proper orientation for expression. The electroporation method of this invention produces stable transfectants that express and carry on their surfaces the chimeric TCR (cTCR).

"Chimeric TCR" means a receptor that is expressed by T cells and that comprises intracellular signaling, transmembrane, and extracellular domains, where the extracellular domain is capable of specifically binding in an MHC unrestricted manner an antigen that is not normally bound by a T-cell receptor in that manner. Stimulation of the T cells by the antigen under proper conditions results in proliferation (expansion) of the cells and/or production of IL-2. The exemplary CD19-specific chimeric receptor of this invention is an example of a chimeric TCR. However, the method is applicable to transfection with chimeric TCRs that are specific for other target antigens, such as chimeric TCRs that are specific for HER2/Neu (Stancovski et al., 1993), ERBB2 (Moritz et al., 1994), folate binding protein (Hwu et al., 1995), renal cell carcinoma (Weitjens et al., 1996), and HIV-1 envelope glycoproteins gp120 and gp41 (Roberts et al., 1994). Other cell-surface target antigens include, but are not limited to, CD20, carcinoembryonic antigen, mesothelin, c-Met, CD56, HERV-K, GD2, GD3, alphafetoprotein, CD23, CD30, CD123, IL-11Ralpha, kappa chain, lambda chain, CD70, CA-125, MUC-1, EGFR and variants, epithelial tumor antigen, and so forth.

In certain aspects, the T cells are primary human T cells, such as T cells derived from human peripheral blood mononuclear cells (PBMC), PBMC collected after stimulation with G-CSF, bone marrow, or umbilical cord blood. Conditions include the use of mRNA and DNA and electroporation. Following transfection the cells may be immediately infused or may be stored. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric receptor is expanded ex vivo. The clone selected for expansion demonstrates the capacity to specifically recognize and lyse CD19 expressing target cells. The recombinant T cells may be expanded by stimulation with IL-2, or other cytokines that bind the common gamma-chain (e.g., IL-7, IL-15, IL-21, and others). The recombinant T cells may be expanded by stimulation with artificial antigen presenting cells. The recombinant T cells may be expanded on artificial antigen presenting cell or with an antibody, such as OKT3, which cross links CD3 on the T cell surface. Subsets of the recombinant T cells may be deleted on artificial antigen presenting cell or with an antibody, such as Campath, which binds CD52 on the T cell surface. In a further aspect, the genetically modified cells may be cryopreserved.

T-cell propagation (survival) after infusion may be assessed by: (i) q-PCR using primers specific for the CAR; and/or (ii) flow cytometry using an antibody specific for the CAR.

This invention also represents the targeting of a B cell malignancy or disorder including B cells, with the cell-surface epitope being CD19-specific using a redirected immune T cell that is TCR$^{neg}$. Malignant B cells are an excellent target for redirected T cells, as B cells can serve as immunostimulatory antigen-presenting cells for T cells. Pre-clinical studies that support the anti-tumor activity of adoptive therapy with donor-derived CD19-specific TCR$^{neg}$ cells bearing a human or humanized CAR include (i) redirected killing of CD19+ targets, (ii) redirected secretion/expression of cytokines after incubation with CD19+ targets/stimulator cells, and (iii) sustained proliferation after incubation with CD19+ target/stimulator cells.

In certain embodiments of the invention, the CAR$^+$TCR$^{neg}$ cells are delivered to an individual in need thereof, such as an individual that has cancer or an infection. The cells then enhance the individual's immune system to attack the respective cancer or pathogenic cells. In some cases, the individual is provided with one or more doses of the antigen-specific CAR$^+$TCR$^{neg}$ cells. In cases where the individual is provided with two or more doses of the antigen-specific CAR$^+$TCR$^{neg}$ cells, the duration between the administrations should be sufficient to allow time for propagation in the individual, and in specific embodiments the duration between doses is 1, 2, 3, 4, 5, 6, 7, or more days.

The source of the allogeneic T cells that are modified to include both a chimeric antigen receptor and that lack functional TCR may be of any kind, but in specific embodiments the cells are obtained from a bank of umbilical cord blood, peripheral blood, human embryonic stem cells, or induced pluripotent stem cells, for example. The different banks will not share the same HLAs, so multiple banks may be employed.

Suitable doses for a therapeutic effect would be at least $10^5$ or between about $10^5$ and about $10^{10}$ cells per dose, for example, preferably in a series of dosing cycles. An exemplary dosing regimen consists of four one-week dosing cycles of escalating doses, starting at least at about $10^5$ cells on Day 0, for example increasing incrementally up to a target dose of about $10^{10}$ cells within several weeks of initiating an intra-patient dose escalation scheme. Suitable modes of administration include intravenous, subcutaneous, intracavitary (for example by reservoir-access device), intraperitoneal, and direct injection into a tumor mass.

A pharmaceutical composition of the present invention can be used alone or in combination with other well-established agents useful for treating cancer. Whether delivered alone or in combination with other agents, the pharmaceutical composition of the present invention can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intra-portal, intrahepatic, peritoneal, subcutaneous, or intradermal administration.

A composition of the present invention can be provided in unit dosage form wherein each dosage unit. e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically acceptable diluent, carrier, or vehicle, where appropriate. The specifications for the novel unit dosage forms of the present invention depend on the particular pharmacodynamics associated with the pharmaceutical composition in the particular subject.

Desirably an effective amount or sufficient number of the isolated transduced T cells is present in the composition and introduced into the subject such that long-term, specific, anti-tumor responses are established to reduce the size of a tumor or eliminate tumor growth or regrowth than would otherwise result in the absence of such treatment. Desirably, the amount of transduced T cells reintroduced into the subject causes a 10%, 20%, 30%, 40%, 50%, 60%, 70%, 80%, 90%, 95%, 98%, or 100% decrease in tumor size when compared to otherwise same conditions wherein the transduced T cells are not present.

Accordingly, the amount of transduced T cells administered should take into account the route of administration and should be such that a sufficient number of the transduced T cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1\times10^6$ to about $1\times10^9$ transduced T cells, even more desirably, from about $1\times10^7$ to about $5\times10^8$ transduced T cells, although any suitable amount can be utilized either above, e.g., greater than $5\times10^8$ cells, or below, e.g., less than $1\times10^7$ cells. The dosing schedule can be based on well-established cell-based therapies (see, e.g., Topalian and Rosenberg, 1987; U.S. Pat. No. 4,690,915), or an alternate continuous infusion strategy can be employed.

These values provide general guidance of the range of transduced T cells to be utilized by the practitioner upon optimizing the method of the present invention for practice of the invention. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on interindividual differences in pharmacokinetics, drug disposition, and metabolism. One skilled in the art readily can make any necessary adjustments in accordance with the exigencies of the particular situation.

VII. Immune System and Immunotherapy

In some embodiments, a medical disorder is treated by transfer of a redirected T cell that elicits a specific immune response. In one embodiment of the present invention. B cell lineage malignancy or disorder is treated by transfer of a redirected T cell that elicits a specific immune response. Thus, a basic understanding of the immunologic responses is necessary.

The cells of the adaptive immune system are a type of leukocyte, called a lymphocyte. B cells and T cells are the major types of lymphocytes. B cells and T cells are derived from the same pluripotent hematopoietic stem cells, and are indistinguishable from one another until after they are activated. B cells play a large role in the humoral immune response, whereas T cells are intimately involved in cell-mediated immune responses. They can be distinguished from other lymphocyte types, such as B cells and NK cells by the presence of a special receptor on their cell surface called the T-cell receptor (TCR). In nearly all other vertebrates, B cells and T cells are produced by stem cells in the bone marrow. T cells travel to and develop in the thymus, from which they derive their name. In humans, approximately 1%-2% of the lymphocyte pool recirculates each hour to optimize the opportunities for antigen-specific lymphocytes to find their specific antigen within the secondary lymphoid tissues.

T lymphocytes arise from hematopoietic stem cells in the bone marrow, and migrate to the thymus gland to mature. T cells express a unique antigen binding receptor on their membrane (T-cell receptor), which can only recognize antigen in association with major histocompatibility complex (MHC) molecules on the surface of other cells. There are at least two populations of T cells, known as T helper cells and T cytotoxic cells. T helper cells and T cytotoxic cells are primarily distinguished by their display of the membrane bound glycoproteins CD4 and CD8, respectively. T helper cells secret various lymphokines that are crucial for the activation of B cells, T cytotoxic cells, macrophages, and other cells of the immune system. In contrast, T cytotoxic cells that recognize an antigen-MHC complex proliferate and differentiate into effector cell called cytotoxic T lymphocytes (CTLs). CTLs eliminate cells of the body displaying antigen, such as virus infected cells and tumor cells, by producing substances that result in cell lysis. Natural killer cells (or NK cells) are a type of cytotoxic lymphocyte that constitutes a major component of the innate immune system. NK cells play a major role in the rejection of tumors and cells infected by viruses. The cells kill by releasing small cytoplasmic granules of proteins called perforin and granzyme that cause the target cell to die by apoptosis.

A B cell identifies pathogens when antibodies on its surface bind to a specific foreign antigen. This antigen/antibody complex is taken up by the B cell and processed by proteolysis into peptides. The B cell then displays these antigenic peptides on its surface MHC class II molecules. This combination of MHC and antigen attracts a matching helper T cell, which releases lymphokines and activates the B cell. As the activated B cell then begins to divide, its offspring (plasma cells) secrete millions of copies of the antibody that recognizes this antigen. These antibodies circulate in blood plasma and lymph, bind to pathogens expressing the antigen and mark them for destruction by complement activation or for uptake and destruction by phagocytes. Antibodies can also neutralize challenges directly, by binding to bacterial toxins or by interfering with the receptors used by viruses and bacteria to infect cells.

NK cells or natural killer cells are defined as large granular lymphocytes that do not express T-cell antigen receptors (TCR) or Pan T marker CD3 or surface immunoglobulins (Ig) B cell receptor but that usually express the surface markers CD16 (FcγRIII) and CD56 in humans, and NK1.1/NK1.2 in certain strains of mice.

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

The T-cell receptor, or TCR, is a molecule found on the surface of T lymphocytes (or T cells) that is generally responsible for recognizing antigens bound to major histocompatibility complex (MHC) molecules. It is a heterodimer consisting of an alpha and beta chain in 95% of T cells, while 5% of T cells have TCRs consisting of gamma and delta chains. Engagement of the TCR with antigen and MHC results in activation of its T lymphocyte through a series of biochemical events mediated by associated enzymes, co-receptors, and specialized accessory molecules. In immunology, the CD3 antigen (CD stands for cluster of differentiation) is a protein complex composed of four distinct chains (CD3γ, CD3δ, and two times CD3ε) in mammals, that associate with molecules known as the T-cell receptor (TCR) and the ζ-chain to generate an activation signal in T lymphocytes. The TCR, ζ-chain, and CD3 molecules together comprise the TCR complex. The CD3γ, CD3δ, and CD3ε chains are highly related cell surface proteins of the immunoglobulin superfamily containing a single extracellular immunoglobulin domain. The transmembrane region of the CD3 chains is negatively charged, a characteristic that allows these chains to associate with the positively charged TCR chains (TCRα and TCRβ). The intracellular tails of the CD3 molecules contain a single conserved motif known as an immunoreceptor tyrosine-based activation motif or ITAM for short, which is essential for the signaling capacity of the TCR.

CD28 is one of the molecules expressed on T cells that provide co-stimulatory signals, which are required for T cell activation. CD28 is the receptor for B7.1 (CD80) and B7.2 (CD86). When activated by Toll-like receptor ligands, the B7.1 expression is upregulated in antigen presenting cells (APCs). The B7.2 expression on antigen presenting cells is constitutive. CD28 is the only B7 receptor constitutively expressed on naive T cells. Stimulation through CD28 in addition to the TCR can provide a potent co-stimulatory signal to T cells for the production of various interleukins (IL-2 and IL-6 in particular).

The strategy of isolating and expanding antigen-specific T cells as a therapeutic intervention for human disease has been validated in clinical trials (Riddell et al., 1992; Walter et al., 1995; Heslop et al., 1996).

Malignant B cells appear to be an excellent targets for redirected T cells, as B cells can serve as immunostimulatory antigen-presenting cells for T cells (Glimcher et al., 1982). Lymphoma, by virtue of its lymph node tropism, is anatomically ideally situated for T cell-mediated recognition and elimination. The localization of infused T cells to lymph node in large numbers has been documented in HIV patients receiving infusions of HIV-specific CD8$^+$ CTL clones. In these patients, evaluation of lymph node biopsy material revealed that infused clones constituted approximately 2%-8% of CD8$^+$ cells of lymph nodes. Lymph node homing might be further improved by co-transfecting T cells with a cDNA construct encoding the L-selection molecule under a constitutive promoter since this adhesion molecule directs circulating T cells back to lymph nodes and is down-regulated by in vitro expansion (Chao et al. 1997). The present invention may provide a method of treating a human disease condition associated with a cell expressing endogenous CD19 comprising infusing a patient with a therapeutically effective dose of the recombinant human CD19-specific CAR expressing cell as described above. The human disease condition associated with a cell expressing endogenous CD19 may be selected from the group consisting of lymphoma, leukemia, non-Hodgkin's lymphoma, acute lymphoblastic leukemia, chronic lymphoblastic leukemia, chronic lymphocytic leukemia, and B cell-associated autoimmune diseases.

Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically split into its acute and chronic forms.

Acute leukemia is characterized by the rapid proliferation of immature blood cells. This crowding makes the bone marrow unable to produce healthy blood cells. Acute forms of leukemia can occur in children and young adults. In fact, it is a more common cause of death for children in the U.S. than any other type of malignant disease. Immediate treatment is required in acute leukemia due to the rapid progression and accumulation of the malignant cells, which then spill over into the bloodstream and spread to other organs of the body. Central nervous system (CNS) involvement is uncommon, although the disease can occasionally cause cranial nerve palsies. Chronic leukemia is distinguished by the excessive build up of relatively mature, but still abnormal, blood cells. Typically taking months to years to progress, the cells are produced at a much higher rate than normal cells, resulting in many abnormal white blood cells in the blood. Chronic leukemia mostly occurs in older people, but can theoretically occur in any age group. Whereas acute leukemia must be treated immediately, chronic forms are sometimes monitored for some time before treatment to ensure maximum effectiveness of therapy.

Furthermore, the diseases are classified into lymphocytic or lymphoblastic, which indicate that the cancerous change took place in a type of marrow cell that normally goes on to form lymphocytes, and myelogenous or myeloid, which indicate that the cancerous change took place in a type of marrow cell that normally goes on to form red cells, some types of white cells, and platelets (see lymphoid cells vs. myeloid cells).

Acute lymphocytic leukemia (also known as acute lymphoblastic leukemia, or ALL) is the most common type of leukemia in young children. This disease also affects adults, especially those aged 65 and older. Chronic lymphocytic leukemia (CLL) most often affects adults over the age of 55. It sometimes occurs in younger adults, but it almost never affects children. Acute myelogenous leukemia (also known as acute myeloid leukemia, or AML) occurs more commonly in adults than in children. This type of leukemia was previously called "acute nonlymphocytic leukemia." Chronic myelogenous leukemia (CML) occurs mainly in adults. A very small number of children also develop this disease.

Lymphoma is a type of cancer that originates in lymphocytes (a type of white blood cell in the vertebrate immune system). There are many types of lymphoma. According to the U.S. National Institutes of Health, lymphomas account for about five percent of all cases of cancer in the United States, and Hodgkin's lymphoma in particular accounts for less than one percent of all cases of cancer in the United States. Because the lymphatic system is part of the body's immune system, patients with a weakened immune system, such as from HIV infection or from certain drugs or medication, also have a higher incidence of lymphoma.

In the 19th and 20th centuries the affliction was called Hodgkin's Disease, as it was discovered by Thomas Hodgkin in 1832. Colloquially, lymphoma is broadly categorized as Hodgkin's lymphoma and non-Hodgkin lymphoma (all other types of lymphoma). Scientific classification of the types of lymphoma is more detailed. Although older classifications referred to histiocytic lymphomas, these are recognized in newer classifications as of B, T, or NK cell lineage.

Autoimmune disease, or autoimmunity, is the failure of an organism to recognize its own constituent parts (down to the sub-molecular levels) as "self," which results in an immune response against its own cells and tissues. Any disease that results from such an aberrant immune response is termed an autoimmune disease. Prominent examples include Coeliac disease, diabetes mellitus type 1 (IDDM), systemic lupus erythematosus (SLE), Sjögren's syndrome, multiple sclerosis (MS), Hashimoto's thyroiditis, Graves' disease, idiopathic thrombocytopenic purpura, and rheumatoid arthritis (RA).

Inflammatory diseases, including autoimmune diseases are also a class of diseases associated with B-cell disorders. Examples of autoimmune diseases include, but are not limited to, acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans. Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, perniciousanemia, rapidly progressive glomerulonephritis, psoriasis, and fibrosing alveolitis. The most common treatments are corticosteroids and cytotoxic drugs, which can be very toxic. These drugs also suppress the entire immune system, can result in serious infection, and have adverse affects on the bone marrow, liver, and kidneys. Other therapeutics that has been used to treat Class III autoimmune diseases to date have been directed against T cells and macrophages. There is a need for more effective methods of treating autoimmune diseases, particularly Class III autoimmune diseases.

VIII. Embodiments of Kits of the Invention

Any of the compositions described herein may be comprised in a kit. In some embodiments, allogeneic CAR$^+$ TCR$^{neg}$ cells are provided in the kit, which also may include reagents suitable for expanding the cells, such as media.

In a non-limiting example, a chimeric receptor expression construct, one or more reagents to generate a chimeric receptor expression construct, cells for transfection of the expression construct, and/or one or more instruments to obtain allogeneic cells for transfection of the expression construct (such an instrument may be a syringe, pipette, forceps, and/or any such medically approved apparatus).

In some embodiments, an expression construct for eliminating endogenous TCR α/β expression, one or more reagents to generate the construct, and/or CAR+ T cells are provided in the kit. In some embodiments, there includes expression constructs that encode zinc finger nuclease(s).

In some aspects, the kit comprises reagents or apparatuses for electroporation of cells.

In some embodiments, the kit comprises artificial antigen presenting cells.

The kits may comprise one or more suitably aliquoted compositions of the present invention or reagents to generate compositions of the invention. The components of the kits may be packaged either in aqueous media or in lyophilized form. The container means of the kits may include at least one vial, test tube, flask, bottle, syringe, or other container means, into which a component may be placed, and preferably, suitably aliquoted. Where there is more than one component in the kit, the kit also will generally contain a second, third, or other additional container into which the additional components may be separately placed. However, various combinations of components may be comprised in a vial. The kits of the present invention also will typically include a means for containing the chimeric receptor construct and any other reagent containers in close confinement for commercial sale. Such containers may include injection or blow molded plastic containers into which the desired vials are retained, for example.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Exemplary Materials and Methods

Human Subjects

Peripheral blood mononuclear cells (PBMC) were obtained from healthy adult volunteer donors who had provided informed consent from Gulf Coast Regional Center (Houston, Tex.) in accordance with the Declaration of Helsinki and participated in research approved by MD Anderson Cancer Center (MDACC).

ZFNs Targeting Constant Regions of α and β TCR

ZFNs containing five or six fingers were assembled from an established archive of pre-validated 2-finger and 1-finger modules as described (Doyon et al., 2008; Isalan et al., 2001). ZFN pairs were designed to bind either a sequence within exon 1 of the TCR α constant region (TRAC: NG_001332.2; ZFNs designated as TRAC-ZFN-1 and TRAC-ZFN-2) or a consensus sequence common to exon 1 of both TCR β constant regions 1 and 2 (TRBC1 and TRBC2: NG_001333.2; ZFNs designated as TRBC-ZFN-1 and TRBC-ZFN-2). Genes encoding the ZFNs were assembled using PCR-based methodology and cloned into a DNA expression plasmid (pVAX; Invitrogen, Carlsbad, Calif.). These plasmids were linearized with XhoI and the RiboMAX Large Scale RNA Production System-T7 (Promega, Madison, Wis.) with ARCA cap analog (Ambion, Austin, Tex.) was used to produce and cap mRNA. After in vitro transcription, poly-adenines were added using a poly A tailing kit (Ambion), the integrity and size of the mRNA species was validated on a denaturing 1% agarose gel with 3-(N-morpholino) propanesulphonic acid (MOPS) buffer, and concentration was measured using a spectrophotometer (BioRad, Hercules, Calif.) at $OD_{260}$. The mRNA was stored at −80° C. in nuclease-free vials for single use.

Flow Cytometry

The following monoclonal antibodies (mAbs) and reagents were used with indicated specificity and the appropriate isotype controls. From BD Biosciences (San Jose, Calif.): phycoerythrin (PE)-conjugated anti-CD3ε (cat #347347, clone SK7), PE-anti-CD19 (cat #555413, clone HIB-19), PE-CD64 (cat #558592, clone 10.1), PE-CD86 (cat #555658, clone 2331), PE-CD137L (cat #559446, clone C65-485). FITC-conjugated anti-CD4 (cat #555346, clone RPA-T4), FITC-anti-CD8 (cat #555634, clone HIT8a), PE-mouse IgG2bκ (cat #555058), and FITC-mouse IgG1 (cat #349041). From Jackson ImmunoResearch (West Grove, Pa.): PE-anti-mouse Fab (H+L) (cat #115-116-146). An Alexa 488-conjugated CAR-specific antibody (clone 136-20-1) that recognizes an epitope within scFv region of CD19RCD28 was generated in the laboratory. TCR Vβ usage was analyzed by a panel of anti-Vβ monoclonal antibodies (IOTest® Beta Mark: Beckman Coulter, Brea, Calif.). The inventors added propidium iodide (Sigma-Aldrich, St. Louis, Mo.) just before collecting cells on a flow-cytometer to exclude dead cells from analysis. Data was acquired on a FACS Calibur (BD Biosciences) using CellQuest version 3.3 (BD Biosciences) and analyzed by FCS Express version 3.00 (De Novo Software. Los Angeles. CA) or FlowJo version 7.6.1 (Tree Star, Inc. Ashland, Oreg.).

Artificial Antigen Presenting Cells

K562-derived aAPC were previously modified by lentiviral transduction to constitutively co-express CD19, CD64, CD86, CD137L, membrane-bound (MB) IL-15, and EGFP (the latter encoded following the emcv IRES element). A clone (#4) was obtained by limiting dilution and numerically expanded for use (Manuri et al., 2010). For some experiments CD3-specific antibody (OKT3; eBioscience, San Diego, Calif.) was used to activate T cells by pulsing the mAb onto the $CD64^+$ (FcR) clone #4 (FIG. 8). Expression of desired transgenes and bound OKT3 was validated weekly by flow cytometry before use in co-culture with T cells.

Propagation of Primary T Cells

T cells derived from human PBMC, isolated by density gradient separation using Ficoll-Paque Plus (GE Healthcare. Pittsburgh, Pa.), were numerically expanded in the presence of 50 IU/mL of recombinant human interleukin-2 ([rhIL-2] added three times a week; Chiron, Emeryville, Calif.) on γ-irradiated (100 Gy) aAPC (clone #4, 1:2 T cell:aAPC ratio) that had been pre-loaded with OKT3. T cells with aAPC were cultured in complete medium (CM) defined as Hyclone-RPMI 1640 (Thermo Fisher Scientific, Waltham, Mass.) supplemented with 2 mmol/L L-glutamine (Glutamax-1; Invitrogen) and 10% heat-inactivated Hyclone-fetal bovine serum (Thermo Fisher Scientific).

Generation and Propagation of $CAR^+$ T Cells

DNA supercoiled plasmids (15 µg of CD19RCD28/pS-BSO and 5 µg of pKan-CMV-SB11) (Davies et al., 2010)

encoding the SB transposon (to stably express CD19RCD28) and the SB transposase (to transiently express SB11) were electro-transferred using an Amaxa Nucleofector II device (Lonza. Basel, Switzerland) at $2 \times 10^7$ PBMC/cuvette as previously described (FIG. 7) (Singh et al., 2008). T cells expressing CD19RCD28 were preferentially propagated in CM by recursive addition every 7 or 14 days of clone #4 (not loaded with OKT3) at 1:2 T cell:aAPC (γ-irradiated to 100 Gy) ratio in the presence of rhIL-2 50 IU/mL, added three times a week.

Electro-Transfer of Messenger RNA Species into Primary or CAR$^+$ T Cells

Six days after stimulation of unmodified T cells with OKT3-loaded clone #4 or 2 to 4 days after the last stimulation of CD19RCD28$^+$ T cells with clone #4, $5 \times 10^6$ T cells were mixed with 2.5 to 10.0 μg of each ZFN mRNA in 100 μL of Human T-Cell Nucleofector solution (Cat #VPA-1002, Lonza) and electroporated using the Nucleofector II device with program T-20. Following electroporation, cells were immediately placed in 2 mL of pre-warmed CM and cultured at 37° C., 5% $CO_2$ for 4 to 6 hours and then 50 IU/mL of rhIL-2 was added with 2 mL of 20% FBS-RPMI. In some experiments, to enhance ZFN-mediated enzymatic activity, after overnight culture, cells were transferred to 30° C., 5% $CO_2$ and cultured for 2 days then returned to 37° C. 5% $CO_2$.

Enrichment of CD3$^{neg}$ T cells

Cells washed with PBS supplemented with 2% FBS and 2 mM EDTA, were incubated for 10 minutes with CD3 microbeads (Cat #130-050-101. MilteneyiBiotec, Auburn, Calif.) at 4° C. After washing twice, cells were passed through an LD column (Cat #130-042-901. MilteneyiBiotec), and the flow-through fraction was collected for further use.

Surveyor Nuclease Assay

The levels of genomic disruption of TRAC TRBC1, and TRBC2 in T cells were determined by Surveyor Nuclease assay (Transgenomics, Omaha, Nebr.) (Guschin et al., 2010). The percent target disruption was quantified by densitometry. The PCR primers used for the amplification of target locus are:

```
TRAC forward,
                            (SEQ ID NO: 1)
5'-GGGCAAAGAGGGAAATGAGA-3'

TRAC reverse,
                            (SEQ ID NO: 2)
5'-CAATGGATAAGGCCGAGACC-3'

TRBC1 forward,
                            (SEQ ID NO: 3)
5'-CTGAACAAGGTGTTCCCACCC-3'

TRBC1 reverse,
                            (SEQ ID NO: 4)
5'-GTGTGCGCTGGTTCCTTTCTT-3'

TRBC2 forward,
                            (SEQ ID NO: 5)
5'-CCTGGCCACAGGCTTCTACC-3'

TRBC2 reverse,
                            (SEQ ID NO: 6)
5'-CCACCTTGTCCACTCTGGCTT-3'
```

$^{51}$Chromium Release Assay

Target cells were labeled with 0.1 mCi of $^{51}$Cr (Perkin Elmer, Boston, Mass.) for 2 hours. After washing thrice with ice-cold CM, labeled cells were diluted and plated at $10^3$ cells/well in 100 μL CM in 96-well v-bottomed plates. T cells were added in 100 μL/well at indicated effector target ratios and the plate was spun (180 g for 3 minutes without brake) to facilitate cell-to-cell contact. After a four hour incubation at 37° C., 5% $CO_2$, 50 μL of supernatants were counted on TopCount (Perkin Elmer, Shelton, Conn.). All assays were performed in triplicate. The percent specific lysis was calculated as follows:

$$((\text{experimental cpm–spontaneous cpm})/(\text{maximum cpm–spontaneous cpm})) \times 100.$$

PKH-26 Dilution Assay

T cells were incubated with 2.0 μM of the red-fluorescent lipophilic dye PKH-26 (Cat #PKH26GL, Sigma-Aldrich) for five minutes at room temperature according to the manufacturer's instructions. Cells, 100% labeled with PKH-26, were stimulated with either OKT3 loaded aAPC or CD19$^+$ aAPC in CM supplemented with 50 IU/mL rhIL-2 (added every-other-day). PKH-26-derived fluorescence was measured by flow cytometry 10 days after stimulation and CD19RCD28$^+$ T cells were revealed using anti-CAR mAb clone 136-20-1.

Example 2

Disruption of the αβ TCR-CD3 Complex on T Cells Using ZFNS

Figures 2A, 2B, 2C:
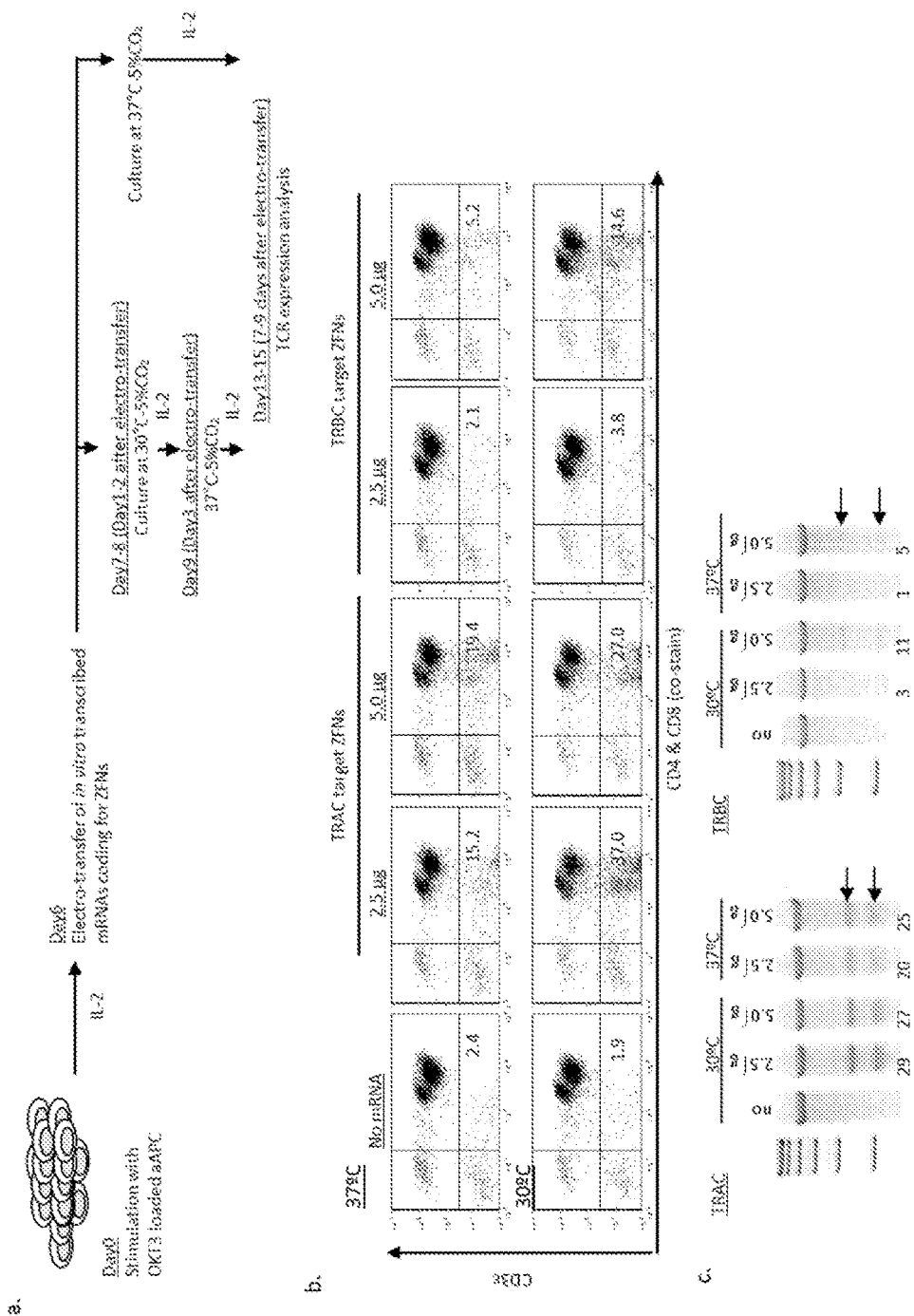
FIG. 2. Disruption of the TCR αβ-CD3 complex in primary T cells.

Two ZFN pairs targeting the constant regions of TCR α (TRAC-ZFN-1 and TRAC-ZFN-2) or TCR β (TRBC-ZFN-1 and TRBC-ZFN-2) (FIG. 1) were developed and tested in primary human T cells propagated ex vivo for six days on OKT3-loaded aAPC (clone #4). Since transient expression of ZFNs is sufficient to mediate gene knockout, the inventors developed a "hit-and-run" delivery strategy to transiently express the ZFNs utilizing electro-transfer of in vitro transcribed mRNA species coding for the ZFN pairs (FIG. 2a). To measure TCR expression the inventors used a mAb specific for CD3ε, which is only present on the cell surface when TCRαβ is expressed. Nine days after electro-transfer, flow cytometric analysis revealed that ZFN pairs targeting TRAC or TRBC eliminated CD3ε expression on primary T cells at levels reaching 19.4% and 5.2%, respectively. The efficiency of TCR knockout correlated with the amount of electro-transferred mRNA (FIG. 2b, upper panel). Although the electro-transfer of mRNA in primary T cells was well-tolerated, they did observe a slight reduction in cell viability that correlated with increasing the amount of introduced mRNA. ZFN-mediated gene disruption has been reported to be more efficient when cells are transiently exposed to mild hypothermia (Doyon et al., 2010). Thus, the inventors cultured T cells for 2 days at 30° C. after electro-transfer. ZFN-mediated disruption of CD3ε was up to 2.4-fold better when electroporated T cells were cultured at 30° C. versus 37° C. Using this approach, 37% and 15% of electroporated T-cells lost expression of CD3ε using the ZFN pair targeting TRAC and TRBC, respectively, (FIG. 2b, lower panel) with no change in the levels of CD3 negative cells in the untransfected samples and without an appreciable decrease in viability (measured by Trypan blue).

To confirm that electroporated T cells had been genetically modified at the intended ZFN target sites (TCR α or β loci), a Surveyor Nuclease assay was performed using specific oligonucleotide primers flanking target sites within TRAC, TRBC1, or TRBC2. Cel-1 nuclease digestion products, representative of genetic changes induced by the ZFNs, were present only after electro-transfer of ZFN pairs and the percent disruption assessed by densitometry correlated with loss of cell surface CD3ε expression (FIG. 2c). These experiments in primary T cells confirmed that ZFNs designed to target TRAC or TRBC lead to permanent disruption of αβTCR expression, as assessed by the Surveyor Nuclease assay and confirmed by flow cytometric analysis of CD3ε.

Example 3

Enrichment of TCR αβ Negative T Cells

Figures 3A, 3B:
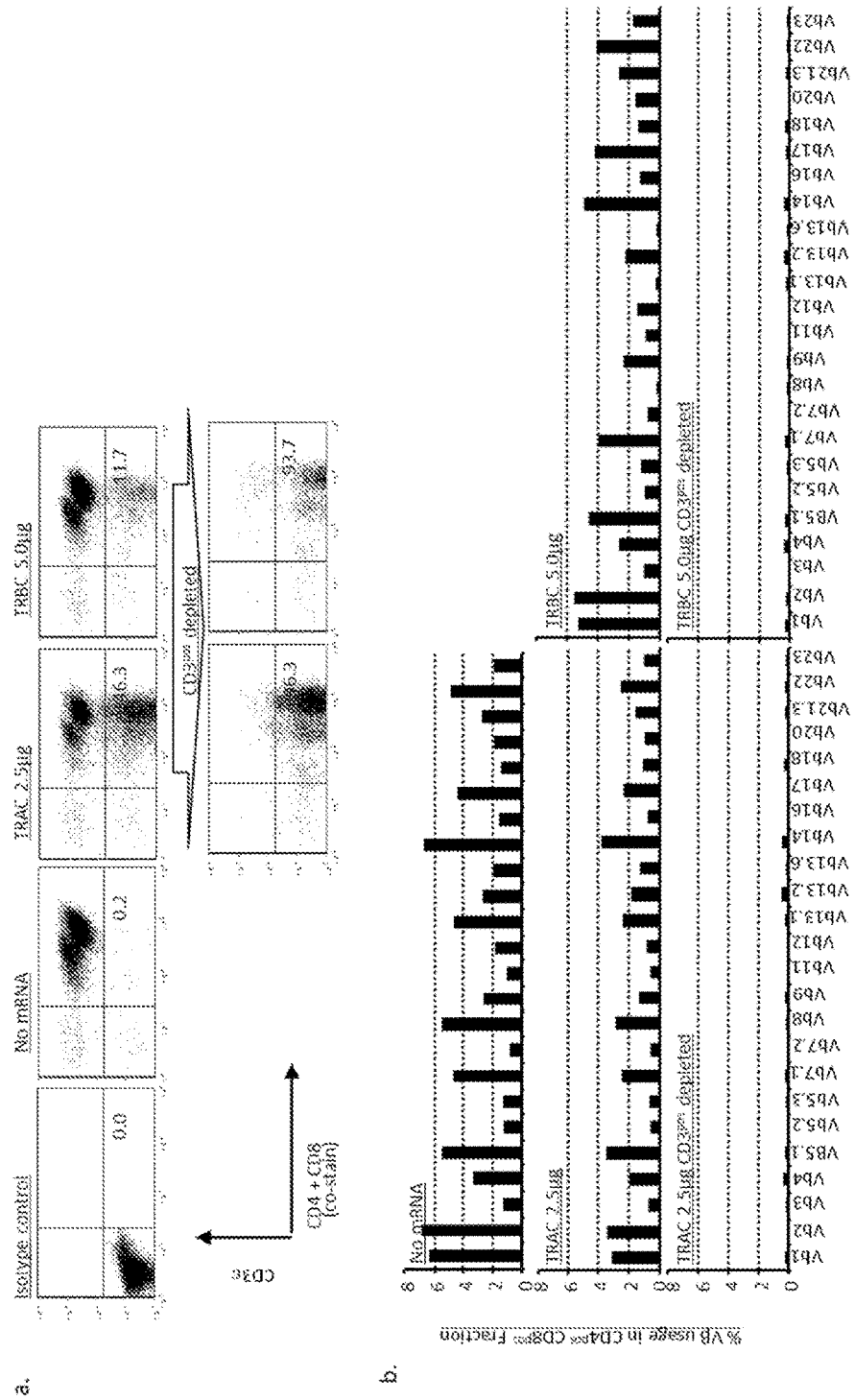

For future clinical applications, rapid and robust methods for isolating sources of TCR disrupted population will be needed. To begin to address this issue, the inventors enriched the TCR/CD3$^{neg}$ population by negative selection using clinically-approved paramagnetic beads and a depletion column. With a single depletion step, the CD3ε$^{neg}$ population was enhanced to over 93% (FIG. 3a). A CD3ε$^{neg}$ population could not be enriched from untransfected control cells. Back-to-back depletion steps resulted in >99% enrichment without skewing the CD4$^+$ or CD8$^+$ T cell subsets (FIG. 9). An analysis of TCR Vβ repertoire in enriched TCR$^{neg}$ T cells via flow cytometry validated the elimination of TCRβ expression from the cell surface (FIG. 3b).

Example 4

Generation of TCR$^{NEG}$ CAR$^+$ T Cells by ZFNS

Figures 4A, 4B:
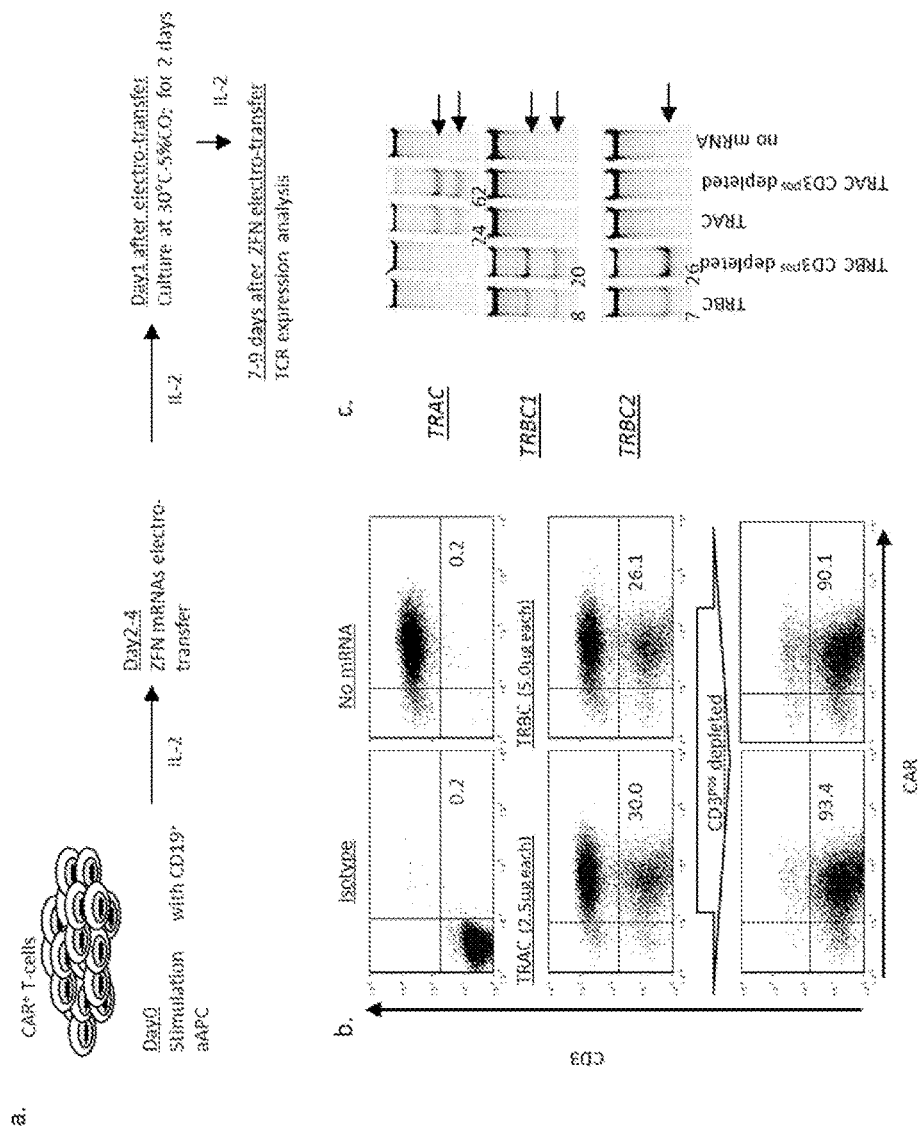
Figures 7A, 7B:
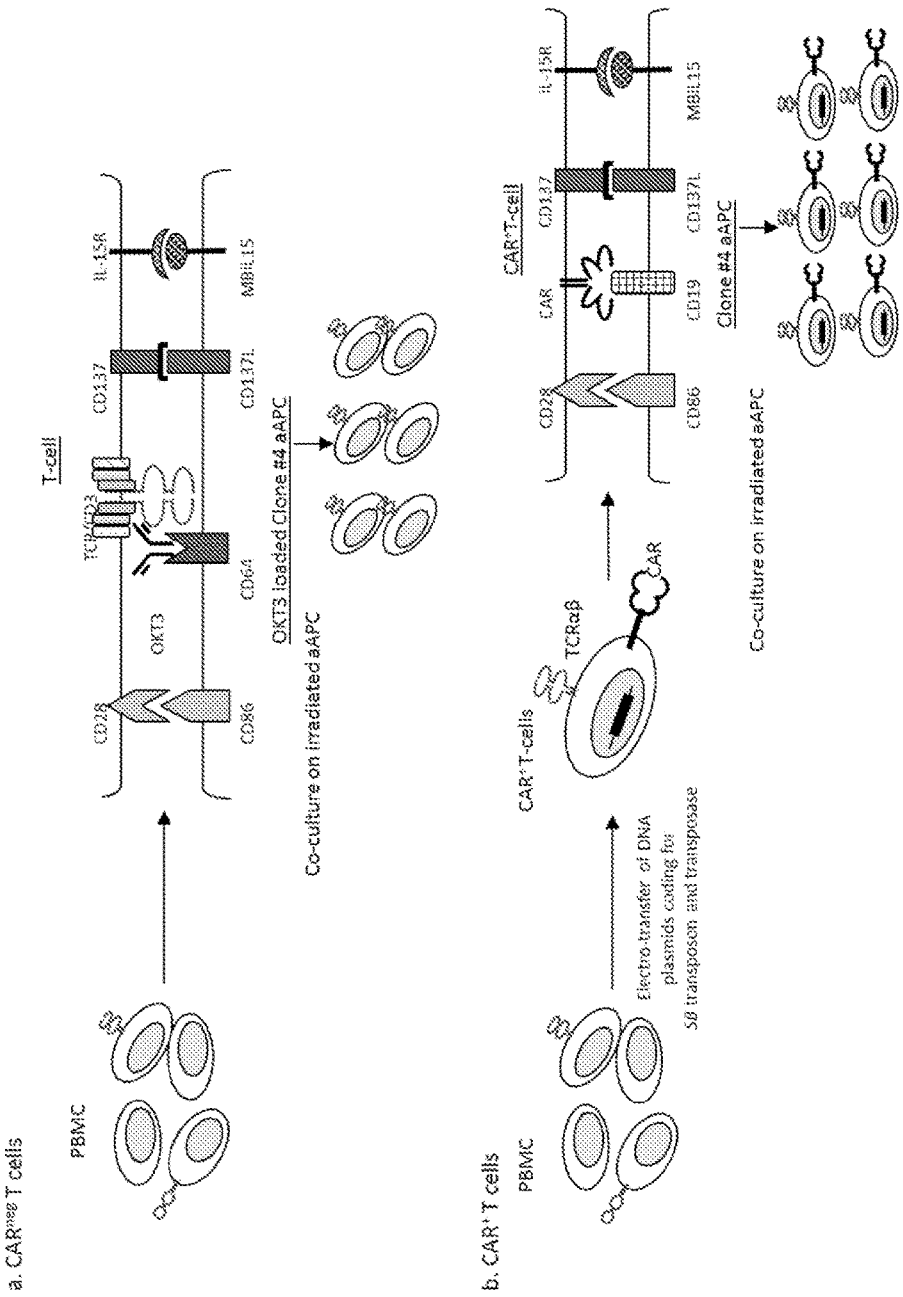

To test the ability of ZFN pairs to knock out TCR αβ expression from allogeneic CD19RCD28$^+$ T cells, the inventors initially genetically modified PBMC to stably express the CD19RCD28 CAR using the SB transposon/transposase system. The CD19RCD28$^+$ T-cell population was specifically propagated by stimulating with γ-irradiated CD19$^+$ aAPC (clone #4) every seven days (FIG. 7b). After four rounds of stimulation, the inventors observed over 90% CAR expression in T cells similar to previously published results (Singh et al. 2008). Within 2 to 4 days after the fifth stimulation with CD19$^+$ aAPC, when T cells were activated, the inventors re-electroporated the cells with mRNA encoding the TRAC or TRBC ZFNs (FIG. 4a). Flow cytometry analysis revealed that up to 30% and 26% of CD19RCD28$^+$ T cells lost CD3ε expression after transfection of the TRAC or TRBC ZFNs, respectively (FIG. 4b). The CD3ε$^{neg}$ population was again readily enriched by paramagnetic beads, and the Surveyor Nuclease assay confirmed that the CD3ε$^{neg}$ population contained a high percentage of modified alleles at the intended ZFN target sites within the TRAC and TRBC loci (FIG. 4c). The frequency of TRBC1 and TRBC2 disruption at the DNA level was approximately 20%-25% and that of TRAC disruption was approximately 60%. These numbers fit with the observed frequencies of CD3ε$^{neg}$ CD19RCD28$^+$ T cells because in each cell only one out of four TRBC alleles (two TRBC1 and two TRBC2) is expressed. Similarly one of two TRAC alleles is expressed in each T cell. Therefore, disruption of the expressed allele is sufficient to achieve the CD3-negative phenotype.

Example 5

Figures 5A, 5B:
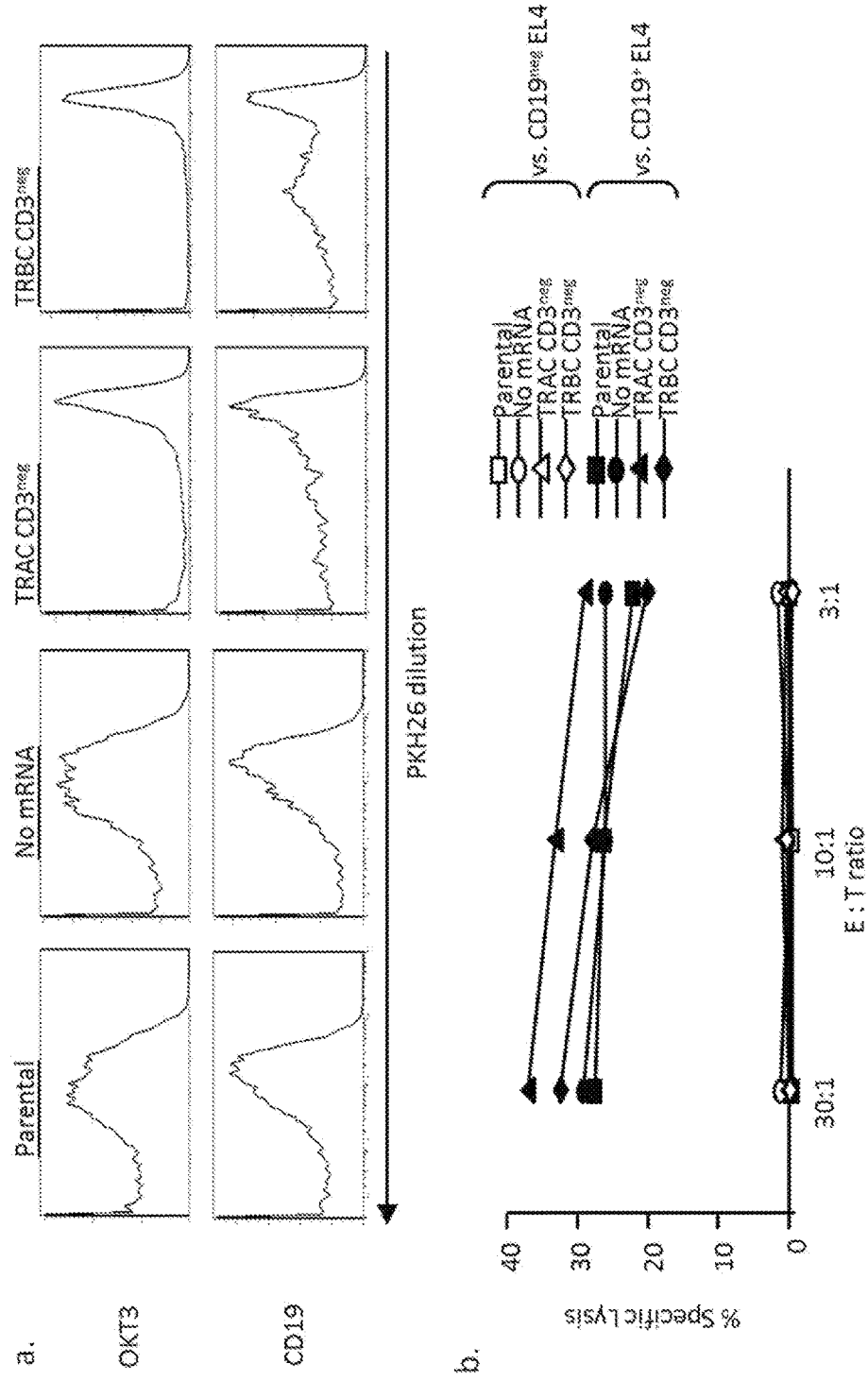

TCR$^{Neg}$CAR$^+$ T Cells do not Respond to TCR Stimulation, but do Maintain CD19 Specificity The inventors anticipated that TCR$^{neg}$CAR$^+$ T cells could not respond to TCR stimulation. To test this, they measured the proliferative response of these cells after stimulation by cross-linking CD3 with OKT3 in comparison to activating CAR for sustained proliferation upon docking with CD19. TCR$^{neg}$CD19RCD28$^+$ T cells proliferated in response to CD19, but not OKT3 (FIG. 5a). Next, the inventors assessed the ability of TCR$^{neg}$CD19RCD28$^+$ T cells to lyse CD19$^+$ target cells in a standard 4-hour $^{51}$Cr release assay (FIG. 5b). The capacity of TCR$^n$CAR$^+$ T cells to specifically lyse CD19 target cells was similar to that observed for TCR$^+$CD19RCD28$^+$ T cells. Together, these data confirmed that the absence of a measurable TCR on TCR$^{neg}$CD19RCD28$^+$ T cells corresponds with abrogation of TCR activity, but does not impact the CAR to activate genetically modified T cells for proliferation and killing.

Example 6

TCR$^{NEG}$CD19RCD28$^+$ T-Cells can be Propagated on CD19-Expressing AAPCS

The inventors confirmed that CD19RCD28$^+$ T cells sustain their proliferative capacity to expand to the cell numbers required for clinical applications. Both the TCR$^{neg}$CD19RCD28$^+$ and parental TCR$^+$CD19RCD28$^+$ T cells exhibited similar growth kinetics in response to stimulation with the CD19 aAPC (FIG. 6). There were no changes in CD3ε expression on TCR$^{neg}$CD19RCD28$^+$ T cells before and after propagation. These data confirm that TCR$^{neg}$CAR$^+$ T cells can be propagated to achieve high enough cell numbers for a single donor-derived, modified T cell pool to be sufficient for subsequent infusion into multiple recipients, as the need arises.

Example 7

Significance of Certain Embodiments of the Invention

Embodiments of the invention show that T cells and indeed CAR$^+$ T cells can be genetically edited by ZFNs to eliminate expression of the endogenous αβ TCR. This has therapeutic implications where donor-derived T cells are infused to achieve an anti-tumor effect. Therapeutic success after allogeneic HSCT is defined as achieving a GVL-effect without causing clinically-significant GVHD (Bleakley et al., 2004). Thus, separation of GVL and GVHD is the crucial issue following engraftment of allogeneic hematopoietic stem cells and strategies to accomplish this are based on infusing desired T-cell effector populations predicted to reduce unwanted allogeneic effects. This includes the adoptive transfer of donor-derived memory T cells employing a narrowed TCR Vβ repertoire compared with naïve T cells (Chen et al., 2004; Foster et al., 2004) or in vitro depletion of T cells activated through allo-antigens (Amrolia et al., 2003; Hartwig et al., 2006; Wehler et al., 2007). CAR$^+$ T cells expressing alloreactive TCRs can be rendered anergic to disparate HLA while maintaining specificity for CD19 (Davies et al., 2010) by blockade of co-stimulatory molecules upon co-culture of genetically modified T cells with stimulator cells expressing disparate HLA. This approach has clinical significance as it can be undertaken in compliance with current good manufacturing practice. An alternative to pre-selection includes conditional ablation of infused allogeneic CAR$^+$ T cells in the event that serious adverse events occur. This has been accomplished by genetic modification of allogeneic T cells to express "suicide genes" such as HSVtk (Bonini et al., 1997), iCasp9 (Straathof et al., 2005), CD20 (Introna et al., 2000), TMPK (Sato et al., 2007), and a modified Fas (Berger et al., 2004) that can be triggered for conditional ablation via the administration of specific molecules (e.g., ganciclovir to HSVtk expressing cells).

The inventors recognized that approaches to selectively deplete T cells expressing undesired αβ TCR may be incomplete and that complete knockout of the endogenous TCR might be advantageous not only to prevent GVHD, but also to prevent the endogenous TCR from adversely affecting CAR function (e.g., through competition for transcription factors). Therefore, the inventors undertook a genetic approach using designer ZFNs to permanently disrupt the α and β constant region sequences in T cells, thereby eliminating TCR expression. Since TCR αβ receptors need to form heterodimers to express a functional cell surface molecule, knocking out either TRAC or TRBC was sufficient to eliminate TCR αβ expression. This is supported by a recent publication showing that a mutation in TRAC gene leads to the loss of TCR αβ expression (Morgan et al., 2011).

ZFNs have been demonstrated to disrupt target gene expression as a consequence of error-prone DNA DSB repair by NHEJ, which in most cases results in a frame shift mutation leading to a premature stop of translation (Santiago et al., 2008). This technology is being evaluated in a pilot clinical trial infusing HIV-resistant T cells generated by ZFN-mediated disruption of the CCR5 co-receptor for HIV-1 (Perez et al., 2008; Holt et al., 2010). ZFNs target and thus disrupt gene expression at the genomic level, which is an advantage over techniques that involve transcriptional repression and require sustained expression of the inhibiting factor (e.g., enforced expression of shRNA to mediate TCR down regulation (Okamoto et al., 2009)). That ZFNs can permanently disrupt gene expression after transient expression (without the inherent dangers of genomic integration) enabled the use of in vitro transcribed mRNA species in a "hit-and-run" manner for electro-transfer of ZFNs into T cells.

Previous reports suggest that T-cell activation mediated through an endogenous TCR is required to obtain a fully functional CAR in a model system using Jurkat cell lines (Bridgeman et al., 2010). In contrast, the inventors observed that knocking out TCR αβ expression from CD19RCD28$^+$ T cells did not appreciably alter the ability of these cells to specifically kill CD19$^+$ targets or proliferate in response to CD19. One reason for this discrepancy other than the difference in host cells may be the use of a $2^{nd}$ generation CAR, which includes signaling not only through CD3ζ (signal 1) but also CD28 (signal 2; co-stimulation) (Maher et al., 2002; Kowolik et al., 2006; Savoldo et al., 2011). Additional inclusion of a CD137 domain, also demonstrated to enhance the function and survival of CD19RCD28$^+$ T cells (Carpenito et al., 2009; Wang et al., 2007), may be tested (Milone et al., 2009). A benefit to expressing TCR with known specificity is that activation through the endogenous immunoreceptor can be used to propagate T cells to achieve an anti-tumor effect mediated by the CAR (Cooper et al., 2005; Pule et al., 2008). It remains to be tested in humans whether coordinated co-stimulation achieved through multiple CAR signaling endodomains will be sufficient to sustain persistence in vivo or if triggering of T cells through TCR is needed. However, the propagation of CD19RCD28$^+$ T cells on aAPC modified to co-express CD19 along with co-stimulatory molecules results in the significant expansion of CAR memory T-cell subsets predicted for prolonged in vivo survival (Numbenjapon et al., 2007; Butler et al., 2011). Therefore, any loss of persistence of TCR$^{neg}$CD19RCD28$^+$ T cells may be off-set by co-stimulatory properties of aAPC and the encoded CD28 intra-cellular domain within the CAR.

Preparing antigen-specific T cells from a third party donor is clinically appealing as these products can be generated, stored, and validated before use and infused to multiple patients immediately as needed (Cooper, 2010). Indeed, third party T cells have been successfully infused into patients with post-transplantation lymphoproliferative diseases (Barker et al., 2010; Haque et al., 2002). Despite the fact that a majority of the viral-antigen specific TCR αβ chains demonstrate cross-reactivity to allo-HLA in vivo (Amir et al., 2010), clinically significant GVHD was not observed. This may be in part due to the ex vivo repetitive antigen stimulation resulting in the emergence of either an oligoclonal or monoclonal TCR αβ repertoire that decreases the chance of T-cell alloreactivity. On the contrary, when the inventors numerically expand CD19RCD28$^+$ T cells through in vitro CD19 stimulation on aAPC independent of TCR stimulation they did not observe skewing of the TCR Vβ usage when measured by a panel of Vβ-specific antibodies. Therefore, elimination TCR αβ expression is needed in a manufacturing process to avoid GVHD upon infusion of allogeneic CAR$^+$ T cells.

TCR$^{neg}$CAR$^+$ T cells can be generated using a genetic approach to remove (a) endogenous undesired TCR with ZFNs and (b) introduce a desired CAR with the SB system, for example. The genetic approaches to introduce mRNA and DNA use a common electro-transfer platform approved for clinical trials. The inventive approach abolishes the danger of GVHD posed by adoptive transfer of large numbers of allogeneic T cells while maintaining desired effector functions mediated by CD19RCD28 CAR to target malignant B cells. This strategy provides an important step to developing a "universal" CAR$^+$ T cell that can be manufactured from one donor and administered on demand to multiple patients. One can also focus on inhibiting rejection of the graft by "hiding" the TCR$^{neg}$CAR$^+$ T cells from the recipient's immune system. This may be accomplished, for example, by genetic modifications including knockout of T-cell MHC and over-expression of MHC homologues known to inhibit NK-cell activity.

Example 8

HLA and TCR Knockout by Zinc Finger Nucleases: Toward "Off-the-Shelf" Allogeneic T-Cell Therapy for CD19$^+$ Malignancies Cell therapy by infusion of T cells can reconstitute immunity to combat pathogens and malignancies. However, the time required to manufacture T cells with the desired properties and in sufficient numbers ex vivo is often incompatible with the treatment window for patients. Furthermore, autologous T cells from patients with advanced disease may have compromised function and be tolerant to desired antigens. In some embodiments, one can infuse allogeneic T cells that avoid immune-mediated rejection caused by host T cells recognizing disparate major or minor histocompatibility antigens on the infused cells. To broaden the application of T cell therapy, it was characterized whether HLA gene expression can be disrupted by designer zinc-finger nucleases (ZFNs), for example. ZFNs comprise a zinc finger DNA-binding domain designed to bind a specific DNA sequence fused to the cleavage domain of FokI endonuclease. Since FokI dimerization is required to introduce a double strand break (DSB), the inventors generated ZFN pairs that flank the intended DNA target sequences in the required spatial conformation. Cellular repair of the DSB by error-prone nonhomologous end joining allows disruption of HLA gene expression. Transfection of ZFN pairs designed to target exon 3 of the HLA-A locus into the human kidney cell line HEK293 resulted in 10% genetic modification of the HLA-A loci. The inventors generated clones of HEK293 cells that showed deletion or insertion mutations within the ZFN binding site of one or both HLA-A alleles leading to early termination of translation. These HLA-A$^{null}$ HEK293 clones evaded HLA-A-restricted lysis by T cell clones, even after interferon-γ and TNF-α treatment was used to upregulate HLA expression. Because only transient expression of ZFNs is needed to disrupt a target gene, the inventors tested the ability to disrupt HLA-A gene expression by electro-transfer of in vitro-transcribed ZFN mRNA into primary T cells. A single administration of the mRNA encoding the ZFNs targeting HLA-A could render over 40% of primary T cells HLA-A negative. The inventors enriched the HLA-A$^{null}$ population by paramagnetic bead separation to obtain a pool of T cells >90% of which lack HLA-A expression. A useful clinical application for HLA$^{null}$ allogeneic T cells is to redirect their specificity independent of HLA via expression of a chimeric antigen receptor (CAR) targeting CD19. Thus, the inventors eliminated HLA-A expression from CD19-specific CAR$^+$ T cells and demonstrated that they (i) evade HLA-A-restricted lysis by T cell clones and (ii) specifically lysed CD19 tumor targets. Finally, to further improve this T cell product and eliminate potential deleterious immune mediated recognition by the endogenous T cell receptor (TCR) on allogeneic CAR$^+$ T cells, the inventors used ZFN pairs targeting the TCR α or the TCR β locus. Transient expression of these ZFNs resulted in permanent disruption of endogenous TCR expression and a highly enriched αβ TCR$^{null}$ cell population could be generated by paramagnetic bead selection. Thus, it is useful to provide allogeneic T cells as "off-the-shelf" biologics that can be infused on demand as "drugs."

Example 9

HLA and TCR Knockout by Zing Finger Nucleases: Toward "Off-the-Shelf" Allogeneic T-Cell Therapy for CD19+ Malignancies CD19 is a lineage-specific cell-surface antigen expressed on B-cell malignancies. T cells can be manufactured to target CD19 independent of HLA molecules by electro-transfer of CD19-specific chimeric antigen receptor (CD19RCD28CAR). This can be useful, given that T cells from patients can be functionally flawed and/or the time to manufacture a T-cell dose may not match the time window for infusion, given the pace of tumor progression.

In FIG. 10, the inventors generate CD19RCD28CAR+ T cells from third party healthy donors that can avoid rejection. In doing so, there is avoidance of unwanted immune reactions mediated by the interaction between HLA and TCR.

The inventors have also used zinc finger nucleases (ZFNs) to achieve elimination of HLA in the genome as well as elimination of the TCR. ZFN comprises two domains: a nuclease domain of FokI restriction enzyme and a designed zinc finger protein (FIG. 11a). A pair of ZFN can induce DNA double strand break (DSB) at a target nucleotide sequence in the genome. Error-prone non-homologous end joining repair of ZFN-mediated DNA DSB leads to complete elimination of target gene expression (FIG. 11b).

The inventors designed a pair of ZFN (ZFN-R and ZFN-L) to induce DSB at a coding sequence of the HLA-A gene. HEK 293 cells (karyotyping analysis showed that this cell line has four copies of chromosome 6, wherein the HLA-A gene is located) were transduced with a pair of ZFN and HLA-A disruption was evaluated by Surveyor Nuclease (CEL-I) assay. HLA-A-targeted ZFNs disrupt the HLA-A locus in up to 10% of HEK293 cells (FIG. 12a). For detailed analysis, the inventors isolated ZFN-transduced HEK293 clones, and they could not detect HLA-A expression in these clones even after IFNγ and TNFα treatment (FIG. 12b). These HEK293 clones evade HLA-A restricted CTL clone attack, when they were pulsed with high dose cognate peptide (FIG. 12c).

HLA-A-targeted ZFNs can also disrupt HLA-A from T cells over 40% when they were expressed from in vitro transcribed mRNA (FIG. 13a). HLA-A$^{null}$ T-cell population can be enriched by simple paramagnetic beads-based sorting (FIG. 13b).

HLA-A-targeted ZFNs also disrupt HLA-A expression from CD19RCD28CAR$^+$ T cells (FIG. 14A). HLA-A$^{null}$CD19RCD28CAR$^+$ T cells evade HLA-A restricted CTL attack (FIG. 14b) but maintain CD19 specificity (FIG. 14c).

TCR expression can also be disrupted from CD19RCD28CAR$^+$ T cells by TCR α or β constant region-targeted ZFN pairs (FIG. 15a). TCR$^{null}$CD19RCD28CAR$^+$ T cells maintain CD19 specificity (FIG. 6b) and also can be propagated on CD19-expressing K562-based artificial antigen presenting cells (FIG. 15c).

TCR and HLA-A expression can be simultaneously disrupted in CD19RCD28CAR$^+$ T cells by treating the cells with both TCR α or β constant region-targeted ZFN pairs and HLA-A-targeted ZFN pairs (FIG. 16).

One can eliminate HLA-A and/or TCR αβ expression from primary T cells and genetically modified T cells by designer ZFNs expressed from electro-transferred mRNA that is amenable to clinical translation. One can enrich HLA$^{null}$ and/or TCR$^{null}$ populations by a single magnetic-beads based selection amenable to clinical translation. The inventors did not observe any adverse effects in ZFN-transduced T cells in terms of cell growth or function.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

PATENTS AND PATENT APPLICATIONS

U.S. Pat. No. 4,690,915
U.S. Pat. No. 6,410,319
U.S. Pat. No. 6,489,458
U.S. Pat. No. 7,109,304

PUBLICATIONS

Altenschmidt et al., *J. Mol. Med.*, 75:259, 1997.
Amir et al., Allo-HLA reactivity of virus-specific memory T cells is common, *Blood*, 115:3146-3157, 2010.

Amrolia et al., Selective depletion of donor alloreactive T cells without loss of antiviral or antileukemic responses, *Blood*, 102:2292-2299, 2003.

Arden et al., Human T-cell receptor variable gene segment families. *Immunogenetics*, 42:455-500, 1995.

Barker et al., Successful treatment of EBV-associated post-transplantation lymphoma after cord blood transplantation using third-party EBV-specific cytotoxic T lymphocytes, *Blood*, 116:5045-5049, 2010.

Barthel and Goldfeld, *J. Immunol.*, 171:3612-3619, 2003.

Berger et al., Pharmacologically regulated Fas-mediated death of adoptively transferred T cells in a nonhuman primate model, *Blood*, 103:1261-1269, 2004.

Bleakley and Riddell, Molecules and mechanisms of the graft-versus-leukaemia effect, *Nat. Rev. Cancer*, 4:371-380, 2004.

Bonini et al., HSV-TK gene transfer into donor lymphocytes for control of allogeneic graft-versus-leukemia, *Science*, 276:1719-1724, 1997.

Bridgeman et al., The optimal antigen response of chimeric antigen receptors harboring the CD3zeta transmembrane domain is dependent upon incorporation of the receptor into the endogenous TCR/CD3 complex. *J. Immunol.*, 184:6938-6949, 2010.

Brocker et al., *Adv. Immunol.*, 68:257, 1998.

Butler et al., Establishment of Antitumor Memory in Humans Using in Vitro-Educated CD8+ T Cells, *Sci. Transl. Med.*, 3:80ra34, 2010.

Carpenito et al., Control of large, established tumor xenografts with genetically retargeted human T cells containing CD28 and CD137 domains, *Proc. Natl. Acad. Sci. U.S.A.*, 106:3360-3365, 2009.

Chao et al., *J. Immunol.*, 159:1686, 1997.

Chen et al. Transfer of allogeneic CD62L− memory T cells without graft-versus-host disease, *Blood*, 103:1534-1541, 2004.

Cooper et al., Development and application of CD19-specific T cells for adoptive immunotherapy of B cell malignancies, *Blood Cells Mol. Dis.*, 33:83-89, 2004.

Cooper et al., Enhanced antilymphoma efficacy of CD19-redirected influenza MP1-specific CTLs by cotransfer of T cells modified to present influenza MP1, *Blood*, 105:1622-1631, 2005.

Cooper, Off-the-shelf T-cell therapy, *Blood*. 116:4741-4743, 2010.

Davies et al., Combining CD19 redirection and alloanergization to generate tumor-specific human T cells for allogeneic cell therapy of B-cell malignancies, *Cancer Res.*, 70:3915-3924, 2010.

Doyon et al., Transient cold shock enhances zinc-finger nuclease-mediated gene disruption, *Nat. Methods*. 7:459-460, 2010.

Doyon et al., Heritable targeted gene disruption in zebrafish using designed zinc-finger nucleases, *Nat. Biotechnol.*, 26:702-708, 2008.

Eshhar et al., *Proc. Natl. Acad Sci. U.S.A.*, 90:720, 1993.

Eshhar, *Cancer Immunol. Immunother.* 45:131, 1997.

Fitzer-Attas et al., *J. Immunol.*, 160:145, 1998.

Foster et al., Human CD62L− memory T cells are less responsive to alloantigen stimulation than CD62L+ naive T cells: potential for adoptive immunotherapy and allodepletion, *Blood*, 104:2403-2409, 2004.

Glimcher et al., *J. Exp. Med.*, 155:445, 1982.

Gross et al., *FASEB J.*, 6:3370, 1992.

Guschin et al., A rapid and general assay for monitoring endogenous gene modification, *Methods Mol. Biol.*, 649:247-256, 2010.

Hackett et al., A transposon and transposase system for human application, *Mol. Ther.*, 18:674-683, 2010.

Haque et al., Treatment of Epstein-Barr-virus-positive post-transplantation lymphoproliferative disease with partly HLA-matched allogeneic cytotoxic T cells, *Lancet*, 360:436-442, 2002.

Hartwig et al., Depletion of alloreactive T cells via CD69: implications on antiviral, antileukemic and immunoregulatory T lymphocytes, *Bone Marrow Transplant.*, 37:297-305, 2006.

Hekele et al., *Int. J. Cancer*, 68:232, 1996.

Heslop et al., *Nat. Med.*, 2:551, 1996.

Holt et al., Human hematopoietic stem/progenitor cells modified by zinc-finger nucleases targeted to CCR5 control HIV-1 in vivo, *Nat. Biotechnol.*, 28:839-847, 2010.

Hwu et al., *Cancer Res.*, 55:3369, 1995.

Introna et al., Genetic modification of human T cells with CD20: a strategy to purify and lyse transduced cells with anti-CD20 antibodies, *Hum. Gene. Ther.*, 11:611-620, 2000.

Isalan and Choo, Rapid, high-throughput engineering of sequence-specific zinc finger DNA-binding proteins, *Methods Enzymol.*, 340:593-609, 2001.

Izsvak et al., Translating Sleeping Beauty transposition into cellular therapies: victories and challenges, *Bioessays*, 32:756-767, 2010.

Jena et al., Redirecting T-cell specificity by introducing a tumor-specific chimeric antigen receptor, *Blood*, 116:1035-1044, 2010.

Kochenderfer et al., Eradication of B-lineage cells and regression of lymphoma in a patient treated with autologous T cells genetically engineered to recognize CD19, *Blood*, 116:4099-4102, 2010.

Kohn et al., CARs on Track in the Clinic, *Mol. Ther.*, 19:432-438, 2011.

Kowolik et al., CD28 costimulation provided through a CD19-specific chimeric antigen receptor enhances in vivo persistence and antitumor efficacy of adoptively transferred T cells. *Cancer Res.*, 66:10995-11004, 2006.

Maher et al., Human T-lymphocyte cytotoxicity and proliferation directed by a single chimeric TCRzeta/CD28 receptor, *Nat. Biotechnol.*, 20:70-75, 2002.

Manuri et al., piggyBac transposon/transposase system to generate CD19-specific T cells for the treatment of B-lineage malignancies. *Hum. Gene Ther.*, 21:427-437, 2010.

Marodon et al., *Blood*, 101:3416-3423, 2003.

Milone et al., *Chimeric receptors containing CD137 signal transduction domains mediate enhanced survival of T cells and increased antileukemic efficacy in vivo, Mol. Ther.*, 17:1453-1464, 2009.

Morgan et al., Mutation in the TCRalpha subunit constant gene (TRAC) leads to a human immunodeficiency disorder characterized by a lack of TCRalphabeta+ T cells, *J. Clin. Invest.*, 121:695-702, 2011.

Moritz et al., *Proc. Natl. Acad. Sci. U.S.A.*, 91:4318, 1994.

Numbenjapon et al., Antigen-independent and antigen-dependent methods to numerically expand CD19-specific CD8+ T cells, *Exp. Hematol.*, 35:1083-1090, 2007.

Okamoto et al., Improved expression and reactivity of transduced tumor-specific TCRs in human lymphocytes by specific silencing of endogenous TCR, *Cancer Res.*, 69:9003-9011, 2009.

Perez et al., Establishment of HIV-1 resistance in CD4+ T cells by genome editing using zinc-finger nucleases, *Nat. Biotechnol.*, 26:808-816, 2008.

Pule et al., Virus-specific T cells engineered to coexpress tumor-specific receptors: persistence and antitumor activity in individuals with neuroblastoma, *Nat. Med.,* 14:1264-1270, 2008.

Remington's Pharmaceutical Sciences, 16*th* ed., Mack, ed., 1980.

Riddell et al., *Science,* 257:238, 1992.

Roberts et al., *Blood,* 84:2878, 1994.

Santiago et al., Targeted gene knockout in mammalian cells by using engineered zinc-finger nucleases, *Proc. Natl. Acad. Sci. U.S.A.,* 105:5809-5814, 2008.

Sato et al., Engineered human tmpk/AZT as a novel enzyme/prodrug axis for suicide gene therapy, *Mol. Ther.,* 15:962-970, 2007.

Savoldo et al., CD28 costimulation improves expansion and persistence of chimeric antigen receptor-modified T cells in lymphoma patients, *J. Clin. Invest.,* 121:1822-1826, 2011.

Scheuermann et al., *Leuk. Lymphoma,* 18:385-397, 1995.

Singh et al., Redirecting specificity of T-cell populations for CD19 using the Sleeping Beauty system, *Cancer Res.,* 68:2961-2971, 2008.

Stancovski et al., *J. Immunol.,* 151:6577, 1993.

Straathof et al., An inducible caspase 9 safety switch for T-cell therapy, *Blood,* 105:4247-4254, 2005.

Topalian and Rosenberg, *Acta Haematol.,* 78 Suppl 1:75-76, 1987.

Uckun et al., *Blood,* 71:13-29, 1988.

Urnov et al., Genome editing with engineered zinc finger nucleases, *Nat. Rev. Genet.,* 11:636-646, 2010.

Walter et al., *N. Engl. J. Med.,* 333:1038, 1995.

Wang et al., Optimizing adoptive polyclonal T cell immunotherapy of lymphomas, using a chimeric T cell receptor possessing CD28 and CD137 costimulatory domains, *Hum. Gene. Ther.,* 18:712-725, 2007.

Wehler et al., Targeting the activation-induced antigen CD137 can selectively deplete alloreactive T cells from antileukemic and antitumor donor T-cell lines, *Blood,* 109:365-373, 2007.

Weijtens et at, *J. Immunol.,* 157:836, 1996.

Williams, Sleeping beauty vector system moves toward human trials in the United States. *Mol. Ther.,* 16:1515-1516, 2008.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. An engineered T cell population wherein cells of the population comprise a zinc finger nuclease that binds an endogenous HLA-A coding sequence, a zinc finger nuclease that binds an endogenous T cell receptor (TCR) β chain coding sequence, and a nucleic acid sequence encoding a recombinant chimeric antigen receptor (CAR) comprising an intracellular signaling domain, a transmembrane domain and an extracellular domain comprising an antigen binding region, and wherein the zinc finger nucleases induce simultaneous deletion in said HLA-A coding sequence and in said TCR β coding sequence such that said cells of the population do not express the endogenous T cell receptor β chain and do not express the endogenous HLA-A coding sequence.

2. The population of cells of claim 1, wherein the endogenous T cell receptor gene is deleted.

3. The population of cells of claim 1, wherein the endogenous HLA-A gene is deleted.

4. The population of cells of claim 1, wherein the antigen binding region is an F(ab')2, Fab', Fab, Fv or scFv.

5. The population of cells of claim 1, wherein the antigen binding region binds a tumor associated antigen.

6. The population of cells of claim 5, wherein the tumor associated antigen is CD19, CD20, carcinoembryonic antigen, alphafetoprotein, CA-125, MUC-1, epithelial tumor antigen, melanoma-associated antigen, mutated p53, mutated ras, HER2/Neu, ERBB2, folate binding protein, HIV-1 envelope glycoprotein gp120, HIV-1 envelope glycoprotein gp41, GD2, CD123, CD23, CD30, CD56, c-Met, mesothelin, GD3, HERV-K, IL-11Ralpha, kappa chain, lambda chain, CSPG4, ERBB2, EGFRvIII, or VEGFR2.

7. The population of cells of claim 1, wherein the antigen binding region binds a pathogen antigen.

8. The population of cells of claim 7, wherein the pathogen antigen is fungal, viral, or bacterial.

9. The population of cells of claim 8, wherein the fungal antigen is from *Aspergillus* or *Candida*.

10. The population of cells of claim 8, wherein the viral antigen is from Herpes Simplex Virus (HSV), Respiratory Syncytial Virus (RSV), Epstein Barr Virus (EBV), Cytomegalovirus (CMV), John Cunningham virus (JC virus), BK virus, or Ebola.

11. The population of cells of claim 1, wherein the intracellular signaling domain is a T-lymphocyte activation domain.

12. The population of cells of claim 1, wherein the intracellular signaling domain comprises CD3ξ, CD28, OX40/CD134, 4-1BB/CD137, FcεRIγ, ICOS/CD278, ILRB/CD122, IL-2RG/CD132, DAP molecules, CD70, cytokine receptor, CD40, or a combination thereof.

13. The population of cells of claim 1, wherein the transmembrane domain comprises IgG4Fc hinge, Fc regions, CD4 transmembrane domain, CD28 transmembrane domain, the CD3ξ transmembrane domain, cysteine mutated human CD3ξ domain, CD16 transmembrane domain, CD8 transmembrane domain, or erythropoietin receptor transmembrane domain.

14. The population of cells of claim 1, wherein the chimeric antigen receptor comprises:
   a) an antigen binding domain from a variable region of antigen-specific monoclonal antibody;
   b) a signaling domain of CD3ξ; and
   c) intracellular signaling domain of CD28, CD137, or both.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gggcaaagag ggaaatgaga                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caatggataa ggccgagacc                                              20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 3
ctgaacaagg tgttcccacc c                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgtgcgctg gttcctttct t                                              21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctggccaca ggcttctacc                                                20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccaccttgtc cactctggct t                                              21

<210> SEQ ID NO 7
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
caacagtgct gtggcctgga gcaacaaatc tgactttgca tgtgcaaacg cc            52

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgctgtcaag tccagttcta cgggctctcg gagaatgacg agtggaccca g             51
```